US011344529B2

(12) United States Patent
van Wyk et al.

(10) Patent No.: US 11,344,529 B2
(45) Date of Patent: May 31, 2022

(54) COMPOSITIONS AND METHODS FOR THE TREATMENT OF METABOLIC CONDITIONS

(71) Applicant: Reven IP HoldCo LLC, Golden, CO (US)

(72) Inventors: Hendrik J. P. van Wyk, Broomfield, CO (US); Peter B. Lange, Golden, CO (US); James Ervin, Novi, MI (US); Brian D. Denomme, Northville, MI (US); Mariette L. van Wyk, Broomfield, CO (US); Peter Pacult, Denver, CO (US); Michael A. Volk, Broomfield, CO (US)

(73) Assignee: REVEN IP HOLDCO LLC, Golden, CO (US)

( * ) Notice: Subject to any disclaimer, the term of this patent is extended or adjusted under 35 U.S.C. 154(b) by 0 days.

(21) Appl. No.: 16/665,795

(22) Filed: Oct. 28, 2019

(65) Prior Publication Data

US 2020/0121640 A1   Apr. 23, 2020

Related U.S. Application Data

(63) Continuation of application No. PCT/US2018/064610, filed on Dec. 7, 2018.

(60) Provisional application No. 62/595,909, filed on Dec. 7, 2017.

(51) Int. Cl.
| | |
|---|---|
| *A61K 31/375* | (2006.01) |
| *A61P 3/00* | (2006.01) |
| *A61K 47/02* | (2006.01) |
| *A61K 9/00* | (2006.01) |
| *A61K 9/08* | (2006.01) |
| *A61K 9/19* | (2006.01) |
| *A61K 31/122* | (2006.01) |
| *A61K 31/197* | (2006.01) |
| *A61K 31/4415* | (2006.01) |
| *A61K 31/455* | (2006.01) |
| *A61K 31/51* | (2006.01) |
| *A61K 31/675* | (2006.01) |
| *A61K 31/714* | (2006.01) |
| *A61K 33/20* | (2006.01) |
| *A61K 45/06* | (2006.01) |

(52) U.S. Cl.
CPC .......... *A61K 31/375* (2013.01); *A61K 9/0014* (2013.01); *A61K 9/0019* (2013.01); *A61K 9/0048* (2013.01); *A61K 9/08* (2013.01); *A61K 9/19* (2013.01); *A61K 31/122* (2013.01); *A61K 31/197* (2013.01); *A61K 31/4415* (2013.01); *A61K 31/455* (2013.01); *A61K 31/51* (2013.01); *A61K 31/675* (2013.01); *A61K 31/714* (2013.01); *A61K 33/20* (2013.01); *A61K 47/02* (2013.01); *A61P 3/00* (2018.01); *A61K 45/06* (2013.01)

(58) Field of Classification Search
CPC .................................................... A61K 31/375
See application file for complete search history.

(56) References Cited

U.S. PATENT DOCUMENTS

| | | | |
|---|---|---|---|
| 5,080,886 A | 1/1992 | Mickle et al. | |
| 6,284,277 B1 | 9/2001 | Bouloumie et al. | |
| 7,282,225 B1 | 10/2007 | Davis et al. | |
| 8,932,574 B2 | 1/2015 | DiBiase et al. | |
| 9,089,511 B2 | 7/2015 | Van Wyk et al. | |
| 9,089,602 B2 | 7/2015 | Van Wyk et al. | |
| 9,572,810 B2 | 2/2017 | Lange et al. | |
| 9,579,312 B2 | 2/2017 | Minowada | |
| 9,775,798 B2 | 10/2017 | Van Wyk et al. | |
| 2002/0176818 A1 | 11/2002 | Fritzberg et al. | |
| 2004/0110684 A1 | 6/2004 | Balligand et al. | |
| 2008/0167345 A1 | 7/2008 | Jones et al. | |
| 2011/0092548 A1 | 4/2011 | Minowada | |
| 2011/0262563 A1 | 10/2011 | van Wyk et al. | |
| 2012/0190731 A1 | 7/2012 | Messina | |
| 2013/0078228 A1 | 3/2013 | Abiko et al. | |
| 2013/0288985 A1 | 10/2013 | Jurkunas | |
| 2015/0079201 A1 | 3/2015 | van Wyk et al. | |
| 2015/0140128 A1 | 5/2015 | van Wyk et al. | |
| 2015/0140129 A1 | 5/2015 | van Wyk et al. | |
| 2015/0196708 A1* | 7/2015 | Mason | A61K 9/19 604/66 |
| 2017/0360696 A1 | 12/2017 | van Wyk et al. | |
| 2018/0057533 A1 | 3/2018 | Oren et al. | |
| 2018/0243332 A1 | 8/2018 | Lange et al. | |

FOREIGN PATENT DOCUMENTS

| | | |
|---|---|---|
| CA | 2408562 A1 | 11/2001 |
| EP | 2324832 B2 | 11/2016 |
| JP | H0959150 A | 3/1997 |

(Continued)

OTHER PUBLICATIONS

Violi et al., Current Development in Atherosclerosis Research, 2006, 117-144, Nova Science Publishers, Inc.(abstract).*
Guaiquil et al., Free Radical Biology & Medicine, 2004, 37(9): 1419-1429.*
Marklund et al., J Gerontol, 1981,36(4); 405-9.*
Heyman et al., "9-Cis Retinoic Acid is a High Affinity Ligand for the Retinoid X Receptor," Cell (Jan. 24, 1992); 68(397-406.
Levy et al., "Long-term culture and expansion of primary human hepatocytes," Nature Biotechnology (Dec. 2015); 33(12):1264-1271.

(Continued)

*Primary Examiner* — Rei Tsang Shiao
(74) *Attorney, Agent, or Firm* — Fox Rothschild LLP

(57) ABSTRACT

The present invention relates to stable therapeutic compositions of pharmaceutical grade acids and pH buffering agents. The present invention also is directed to methods of treatment for mitochondrial disorders, metabolic conditions, diabetic conditions, and cardiovascular conditions, by administration of compositions of the present disclosure.

28 Claims, 8 Drawing Sheets

(56) References Cited

FOREIGN PATENT DOCUMENTS

| KR | 19990067325 | A  | 8/1999  |
|----|-------------|----|---------|
| WO | 200189520   | A2 | 11/2001 |
| WO | 2005/044176 | A2 | 5/2005  |
| WO | 2007051431  | A3 | 6/2007  |
| WO | 2011013138  | A1 | 2/2011  |
| WO | 2017143446  | A1 | 8/2017  |

OTHER PUBLICATIONS

International Search Report and Written Opinion dated Sep. 16, 2020 for PCT International Application No. PCT/US2020/37398 (23 pages).
Extended European Search Report dated Aug. 13, 2021 issued in European Patent Application No. 18886422.7 (7 pages).
Non-FInal Office Action dated Aug. 23, 2021 issued in U.S. Appl. No. 16/770,807 (10 pages).
Search Report and Written Opinion dated Dec. 13, 2021 issued in Singapore Patent Application No. 11202005158P (8 pages).
Notice of Preliminary Rejection dated Mar. 18, 22022 issued in Korean Patent Application No. 10-2020-7019679 (8 pages).

\* cited by examiner

Figure 6. Subject 2 Dose 1, AS Day 1: pH and HCO3- Response
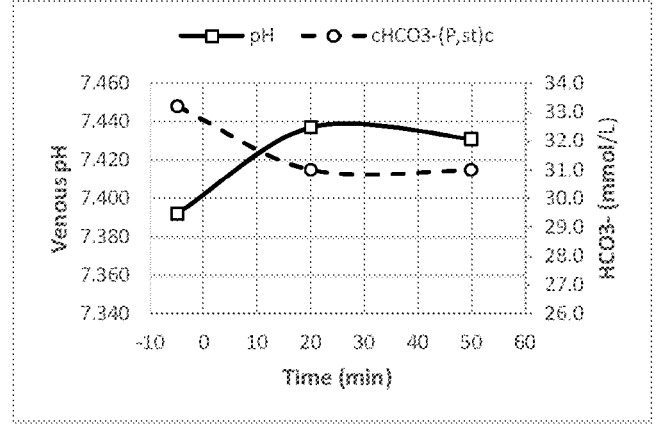
Figure 7. Subject 2 Dose 1, AS DAY 1: sO2, pCO2, pO2 Response
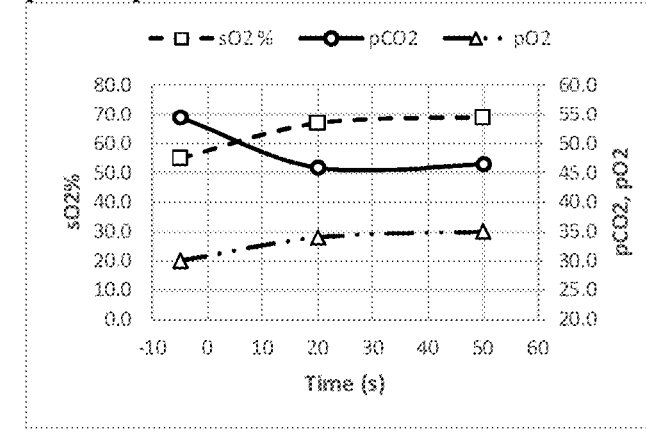
Figure 8. Subject 2 Dose 4, ASVM Day 6: pH and HCO3- Response
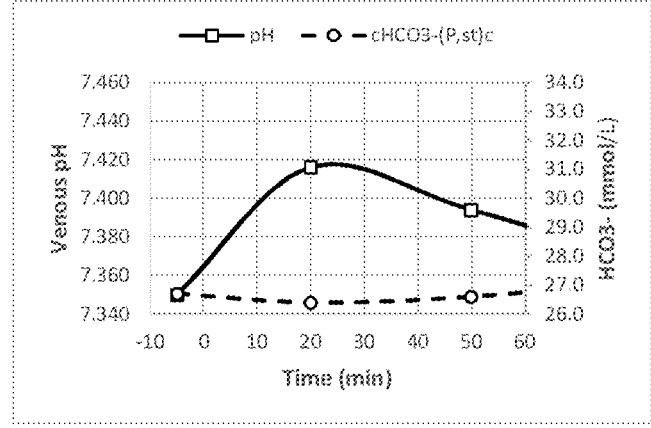

Figure 9. Subject 2 Dose 4, ASVM Day 6: sO2, pCO2, pO2 Response
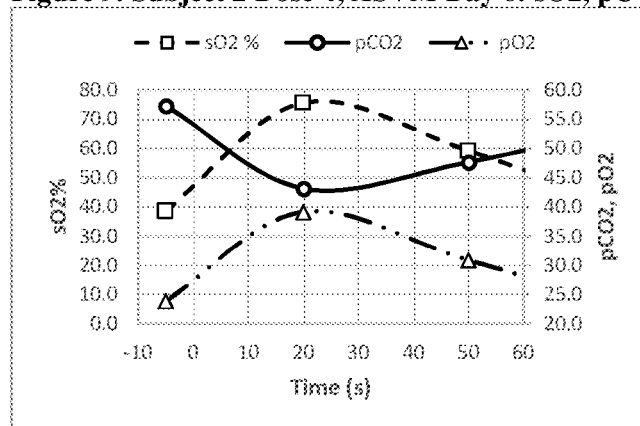
Figure 10. Subject 2 Dose 5, ASVM Day 8: pH and HCO3- Response
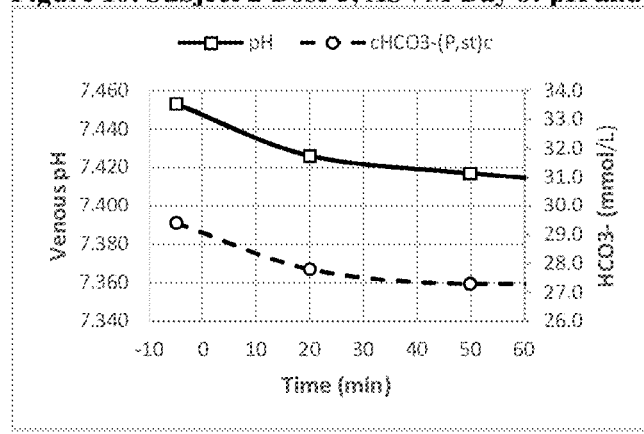
Figure 11 – Subject 2 Dose 5, ASVM Day 8: sO2, pCO2, pO2 Response
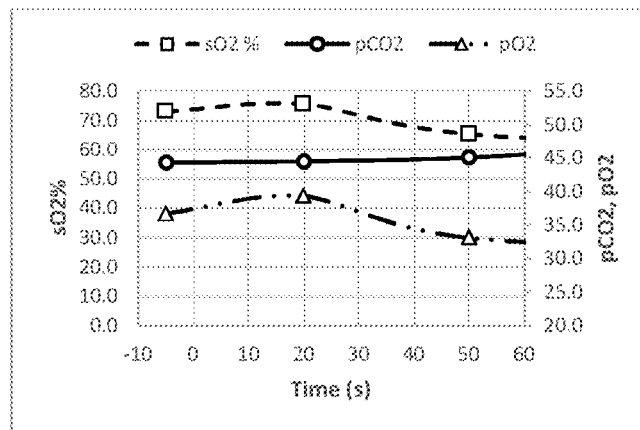

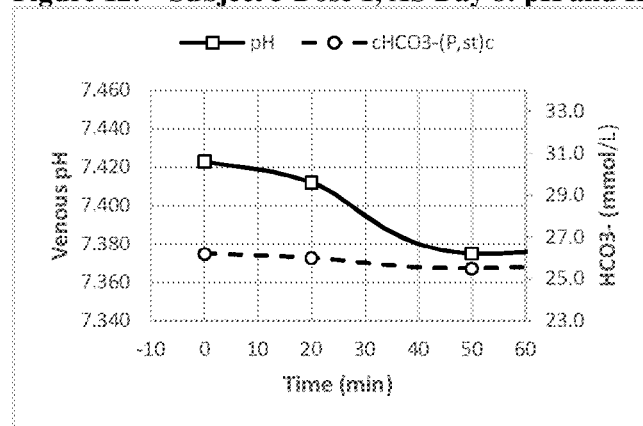
Figure 12. – Subject 3 Dose 1, AS Day 8: pH and HCO3- Response
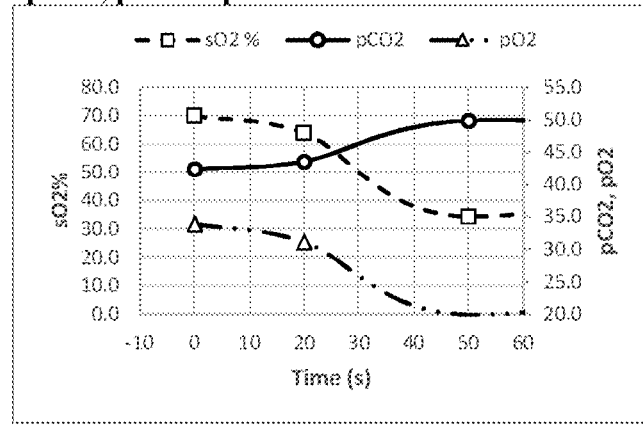
Figure 13. – Subject 3 Dose 1, AS Day 8: sO2, pCO2, pO2 Response

COMPOSITIONS AND METHODS FOR THE TREATMENT OF METABOLIC CONDITIONS

CROSS-REFERENCE TO RELATED APPLICATIONS

This application is a Continuation of International Patent Application No. PCT/US2018/064610, filed Dec. 7, 2018, which claims priority to U.S. Provisional Patent Application No. 62/595,909, filed Dec. 7, 2017, the disclosures of which are incorporated herein by reference.

FIELD OF THE INVENTION

The present invention relates to stable therapeutic compositions comprising pharmaceutical grade acids and pH buffering agents. The present invention also is directed to methods of treatment for conditions and disorders characterized by mitochondrial dysfunction, metabolic conditions, diabetic conditions, cardiovascular conditions, and bone and tissue modeling dysfunction, comprising administration of compositions of the present disclosure.

BACKGROUND OF THE INVENTION

Homeostasis is the ability of an organism to maintain a condition of equilibrium or stability within its internal environment, particularly when faced with external changes. Some examples of homeostatically-controlled systems in humans include the regulation of a constant body temperature, blood glucose levels, and extracellular ionic species concentrations. Acid-base homeostasis relates to the proper balance of acids and bases in extracellular fluids, i.e., the pH of the extracellular fluid. In humans, the pH of plasma is approximately 7.4, and is tightly maintained around that value by three interconnected control systems: 1) buffering agents, including bicarbonate, phosphate, and proteins, 2) the respiratory system, which impacts the partial pressure of carbon dioxide in blood plasma, and 3) the renal system, which excretes waste acids and bases. Acid homeostasis is also influenced by metabolic load, which serves as a primary source of acid in the body. For instance, a high glucose diet can increase total acid burden from metabolic sources, to place a bigger burden on acid homeostasis control mechanisms.

Inefficiencies in these control systems and factors, which increase acid, such as from metabolic sources, may gradually result in unstable internal environments that increase the risk of illness, or exacerbate existing conditions. These inefficiencies may be caused by natural aging processes or may be self-inflicted through various lifestyle choices. For example, a high-glucose diet and a sedentary lifestyle can lead, over time, to the development of insulin insensitivity and type 2 diabetes. Diabetes is associated with other conditions such as obesity, hypertension, hyperlipidemia, fatty liver disease, nephropathy, neuropathy, renal failure, retinopathy, diabetic ulcer, cataracts, insulin resistance syndrome, cachexia, diabetic foot ulcers and diabetic leg ulcers.

Cardiovascular diseases may also be caused by a poor diet and sedentary lifestyle, and include coronary heart disease (heart attacks), cerebrovascular disease, raised blood pressure (hypertension), peripheral artery disease, rheumatic heart disease, congenital heart disease and heart failure. Such dysfunctional conditions of the heart, arteries, and veins impair the supply of oxygen to vital life-sustaining organs, including the brain and the heart itself.

Heart attacks and strokes are mainly caused by a blockage in the inner walls of the blood vessels that prevents blood from flowing to the heart or the brain. Arteriosclerosis (also called atherosclerosis) is a condition involving excess buildup of fat or plaque deposits, respectively, that cause narrowing of the veins that supply oxygenated blood to the tissues. In arteries serving the heart for instance, this may lead to ischemic heart disease, an obstruction of blood flow to the heart. Excess fat or plaque buildup may also cause high blood pressure (hypertension), a disease known as "The Silent Killer" because the first warning sign is an angina attack, a deadly heart attack or a stroke. Kidney disorders, obesity, diabetes, smoking, excess alcohol, stress, and thyroid and adrenal gland problems can also exacerbate a high blood pressure condition.

These conditions and many others are brought on by inefficient, ineffective, or over-stressed homeostatic processes. Over time, the resulting imbalances cause damage at the cellular and intracellular level. Often the mechanisms for cellular repair are so compromised that the cells cannot recover, or the mechanisms that cause the damage simply overwhelm the cell. The clinical significance of the damage generated in living cells is manifested in a diseased cell, or symptoms of an underlying condition. It would be beneficial to develop methods to facilitate the inhibition of cellular damage or boost recovery. The presently disclosed subject matter addresses, in whole or in part, these and other needs in the art.

SUMMARY OF THE INVENTION

It is therefore an object of the invention to provide solutions to the aforementioned needs.

To this end, the present disclosure provides a stable therapeutic composition formulated for intravenous administration to a subject, comprising an intravenous buffer solution, comprising at least one pharmaceutical grade acid and at least one pharmaceutical grade pH buffering agent in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7.

In some embodiments, the pharmaceutical grade acid is hydrochloric acid, ascorbic acid, acetic acid, (other physiologically acceptable acids), or a combination thereof. In some embodiments, the at least one pH buffering agent is sodium bicarbonate, a phosphate, organic acid, organic amine, ammonia, citrate buffer, a synthetic buffer creating specific alkaline conditions (e.g., tris-hydroxymethyl amino methane), (other physiologically acceptable buffers), or a combination thereof.

In some embodiments, the composition further comprises one or more ingredients selected from the group consisting of vitamins, salts, acids, amino acids or salts thereof, and stabilized oxidative species. In some embodiments, the composition further comprises ascorbic acid. In some embodiments, the composition comprises dehydroascorbic acid In some embodiments, the composition comprises other recognized antioxidant defense compounds, including non-enzymatic compounds, such as tocopherol (aTCP), coenzyme Q10 (Q), cytochrome c (C) and glutathione (GSH), and enzymatic components including manganese superoxide dismutase (MnSOD), catalase (Cat), glutathione peroxidase (GPX), phospholipid hydroperoxide glutathione peroxidase (PGPX), glutathione reductase (GR); peroxiredoxins (PRX3/5), glutaredoxin (GRX2), thioredoxin (TRX2) and thioredoxin reductase (TRXR2). In some embodiments, the composition further comprises one or more of a sodium salt, a magnesium salt, a potassium salt, and a calcium salt. In some embodiments, the composition further comprises one or more of a B vitamin, vitamin C, and vitamin K.

In some embodiments, the composition is formulated in hypotonic, isotonic, or hypertonic form. In some embodiments, the composition is formulated for intravenous, bolus, dermal, oral, otic, suppository, buccal, ocular, or inhalation delivery. In some embodiments, the composition is formulated as a topical liquid, gel, or paste. In some embodiments, the composition is formulated for ocular administration in the form of eye drops. In some embodiments, the composition is lyophilized or frozen. In some embodiments, the composition is stored in a spectral-blocking vial. In some embodiments, the composition is formed by combining components from two or more vials.

In another aspect, the present disclosure provides a stable therapeutic composition formulated for intravenous administration to a subject comprising pharmaceutical grade 900±90 mg of L-Ascorbic Acid; 63.33±6.33 mg Thiamine HCl; 808±80.8 mg of Magnesium Sulfate; 1.93±0.193 mg of Cyanocobalamin; 119±11.9 mg of Niacinamide; 119±11.9 mg of Pyridoxine HCl; 2.53±0.253 mg of Riboflavin 5'Phosphate; 2.93±0.293 mg of Calcium D-Pantothenate; 840±84 mg of Sodium Bicarbonate; 4.5±0.45 mM of HCl; and water in an amount to obtain a final composition volume of 20 mL. In one embodiment of the invention, the composition further comprises 100±10 mg of dehydroascorbic acid.

In another aspect, the present disclosure provides a method of treating or ameliorating acidosis in a subject, the method comprising administering to the subject a stable therapeutic composition comprising an intravenous buffer solution comprising at least one pharmaceutical grade acid and at least one pharmaceutical grade pH buffering agent in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7.

In yet another aspect, the present disclosure provides a method of treating or ameliorating base excess in a subject, the method comprising administering to the subject a stable therapeutic composition comprising an intravenous buffer solution comprising at least one pharmaceutical grade acid and at least one pharmaceutical grade pH buffering agent in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7.

In yet another aspect, the present disclosure provides a method of elevating blood oxygen in a subject, the method comprising administering to the subject a stable therapeutic composition comprising an intravenous buffer solution comprising at least one pharmaceutical grade acid and at least one pharmaceutical grade pH buffering agent in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7. In one embodiment of the invention, the method comprises elevating the pO2 in the venous blood in a subject.

In still a further aspect, the present disclosure provides a method of treating or ameliorating a mitochondrial disorder, metabolic disorder, a condition associated with diabetes or a cardiovascular dysfunction in a subject in need thereof, the method comprising administering to the subject a stable therapeutic composition comprising an intravenous buffer solution comprising at least one pharmaceutical grade acid and at least one pharmaceutical grade pH buffering agent in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7.

In some embodiments, the metabolic disorder is diabetes, insulin resistance, glucose intolerance, hyperglycemia, hyperinsulinemia, obesity, hyperlipidemia, or hyperlipoproteinemia. In some embodiments, the condition associated with diabetes is hypertension, hyperlipidemia, fatty liver disease, nephropathy, neuropathy, renal failure, retinopathy, diabetic ulcer, cataracts, insulin resistance syndromes and cachexia. In some embodiments, the cardiovascular dysfunction is coronary heart disease, cerebrovascular disease, hypertension, peripheral artery disease, occlusive arterial disease, angina, rheumatic heart disease, congenital heart disease, heart failure, cardiac insufficiency, palpitations, supraventricular tachycardia, fibrillation, faintness, dizziness, fatigue, migraine, high levels of total blood cholesterol and/or LDL cholesterol, low level of HDL cholesterol, high level of lipoprotein, infections of the heart such as carditis and endocarditis, diabetic ulcer, thrombophlebitis, Raynaud's disease, anorexia nervosa, claudication, gangrene, atherosclerosis and peripheral artery disease. In some embodiments, the mitochondrial disorder is a neurodegenerative disorder, a cardiovascular disease, a metabolic syndrome, an autoimmune disease, a neurobehavioral or psychiatric disease, a gastrointestinal disorder, a fatiguing illness, a chronic musculoskeletal disease, or a chronic infection. In some embodiments, the ocular condition is glaucoma, macular degeneration, eye floaters, ocular lens stiffening, or light sensitivity.

In some embodiments, the composition further comprises dehydroascorbic acid. In some embodiments, the composition further comprises one or more of a magnesium ion source, a potassium ion source, and a calcium ion source. In some embodiments, the composition further comprises one or more of a B vitamin, vitamin C, and vitamin K. In some embodiments, the composition further comprises other recognized antioxidant defense compounds including nonenzymatic compounds such as tocopherol (aTCP), coenzyme Q10 (Q), cytochrome c (C) and glutathione (GSH), and enzymatic components including manganese superoxide dismutase (MnSOD), catalase (Cat), glutathione peroxidase (GPX), phospholipid hydroperoxide glutathione peroxidase (PGPX), glutathione reductase (GR); peroxiredoxins (PRX3/5), glutaredoxin (GRX2), thioredoxin (TRX2) and thioredoxin reductase (TRXR2).

In some embodiments, the composition is formulated in hypotonic, isotonic, or hypertonic form. In some embodiments, the composition is administered intravenously, by bolus, dermally, orally, otically, via suppository, buccally, ocularly, or via inhalation.

In some embodiments, the administering comprises introducing said composition by infusion over a period of about 1 minute to about 1 hour, and said infusion is repeated as necessary over a period of time selected from about 1 day to about 1 year.

In another aspect, the present disclosure provides a method of modifying the metabolism of a subject, the method comprising administering to the subject a stable therapeutic composition comprising an intravenous buffer solution comprising at least one pharmaceutical grade acid and at least one pharmaceutical grade pH buffering agent, in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7.

In another aspect, the present disclosure provides a method of treating a central nervous system disorder in a subject in need thereof, the method comprising administering to the subject a stable therapeutic composition comprising an intravenous buffer solution comprising at least one pharmaceutical grade acid and at least one pharmaceutical grade pH buffering agent, in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7.

In another aspect, the present disclosure provides a method of treating chronic wounds of a subject, the method comprising administering to the subject a stable therapeutic composition comprising an intravenous buffer solution comprising at least one pharmaceutical grade acid and at least one pharmaceutical grade pH buffering agent, in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7.

In another aspect, the present disclosure provides a method of enhancing mental or physical performance of a subject, the method comprising administering to the subject a stable therapeutic composition comprising an intravenous buffer solution comprising at least one pharmaceutical grade acid and at least one pharmaceutical grade pH buffering agent, in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7.

In another aspect, the present disclosure provides a method of reducing lactate burden of a subject, the method comprising administering to the subject a stable therapeutic composition comprising an intravenous buffer solution comprising at least one pharmaceutical grade acid and at least one pharmaceutical grade pH buffering agent, in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7. In one embodiment of the invention, the lactate burden is acidosis, sepsis, or multiple system atrophy (MSA). In another embodiment, the lactate burden is the result of physical exertion.

In another aspect, the present disclosure provides a method of improving hypoxic stress of a subject, the method comprising administering to the subject a stable therapeutic composition comprising an intravenous buffer solution comprising at least one pharmaceutical grade acid and at least one pharmaceutical grade pH buffering agent, in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7.

In another aspect, the present disclosure provides a method of removing vascular plaque from the arteries of a subject, the method comprising administering to the subject a stable therapeutic composition comprising an intravenous buffer solution comprising at least one pharmaceutical grade acid and at least one pharmaceutical grade pH buffering agent, in a sterile aqueous solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7.

In some embodiments of the invention, in the methods of the invention provide a buffer solution that is sufficient to reduce the physiological bloodstream pH of a subject by 0.01 to 1.1. In other embodiments of the invention, the buffer solution is sufficient to reduce the physiological bloodstream pH of a subject by 0.015 to 0.075. In other embodiments of the invention, the buffer solution is sufficient to reduce the physiological bloodstream pH of a subject by 0.02 to 0.05. In other embodiments of the invention, the buffer solution is sufficient to reduce the physiological bloodstream pH of a subject by 0.01 to 0.15. In other embodiments of the invention, the buffer solution is sufficient to reduce the physiological bloodstream pH of a subject by 0.01 to 0.2. In other embodiments of the invention, the buffer solution is sufficient to reduce the physiological bloodstream pH of a subject by 0.02 to 0.05. In other embodiments of the invention, the buffer solution has a buffer capacity sufficient to sustain the reduction of the physiological bloodstream pH of the subject for between 1 minute and 1 week. In other embodiments of the invention, the buffer solution has a buffer capacity sufficient to sustain the reduction of the physiological bloodstream pH of the subject for between 1 minute and 1 hour.

In one embodiment of any of the methods of the invention, the subject is a human or veterinary subject.

In another aspect, the present disclosure provides a kit comprising (a) a first vial containing a stable therapeutic composition comprising a buffer solution comprising at least one pharmaceutical grade acid and at least one pharmaceutical grade pH buffering agent, wherein the buffer solution is sufficient to reduce the physiological bloodstream pH of a subject by 0.1 to 1.1, and wherein the buffer solution has a buffer capacity sufficient to sustain the reduction of the physiological bloodstream pH of the subject for between 1 minute and 1 week; and (b) instructions for use.

In another aspect, the present disclosure provides a kit comprising (a) a first vial containing an intravenous buffer solution comprising at least one pharmaceutical grade acid in a sterile aqueous solution;
(b) a second vial containing at least one pharmaceutical grade pH buffering agent in a sterile aqueous solution, wherein, when combined, the contents of the two vials form an intravenous buffer solution, wherein the concentration of the pharmaceutical grade acid and the pharmaceutical grade pH buffering agent in the buffer solution is sufficient to provide a total titratable acid content of from 60 mmol/L to 3000 mmol/L when administered to a subject, and wherein the selection of the pharmaceutical grade acid and the pharmaceutical grade pH buffering agent is effective to provide a buffer solution pH of between 4 and 7.7; and (c) instructions for use.

The details of one or more embodiments of the invention are set forth in the description below. Other features, objectives, and advantages of the invention will be apparent from the description and from the claims.

BRIEF DESCRIPTION OF THE FIGURES

The accompanying drawings, which are incorporated herein and constitute part of this specification, illustrate the presently preferred embodiments of the invention, and, together with the general description above and the detailed description given below, serve to explain the features of the invention. In the drawings:

FIGS. 6, 7, 8, 9, 10 and 11 show a graphic representation of the pH and $HCO_3^-$ response (FIG. 6—Acid Shifting Composition; Dose 1, Day 1); $sO_2$, $pCO_2$, $pO_2$ response (FIG. 7—Acid Shifting Composition; Dose 1, Day 1); pH and $HCO_3^-$ response (FIGS. 8—Acid Shifting Composition with Vitamins and Minerals; Dose 4, Day 6); $sO_2$, $pCO_2$, $pO_2$ response (FIG. 9—Acid Shifting Composition with Vitamins and Minerals; Dose 4, Day 6); pH and $HCO_3^-$ response (FIGS. 10—Acid Shifting Composition with Vitamins and Minerals; Dose 5, Day 8); and $sO_2$, $pCO_2$, $pO_2$ response (FIG. 11—Acid Shifting Composition with Vitamins and Minerals; Dose 5, Day 8) of Subject 2, after administration of the therapeutic composition.

FIGS. 12 and 13 show a graphic representation of the pH and $HCO_3^-$ response (FIG. 12—Acid Shifting Composition; Dose 1, Day 8); and $sO_2$, $pCO_2$, $pO_2$ response (FIG. 9—Acid Shifting Composition; Dose 1, Day 8) of Subject 3, after administration of the therapeutic composition.

DETAILED DESCRIPTION OF THE INVENTION

Figure 1:
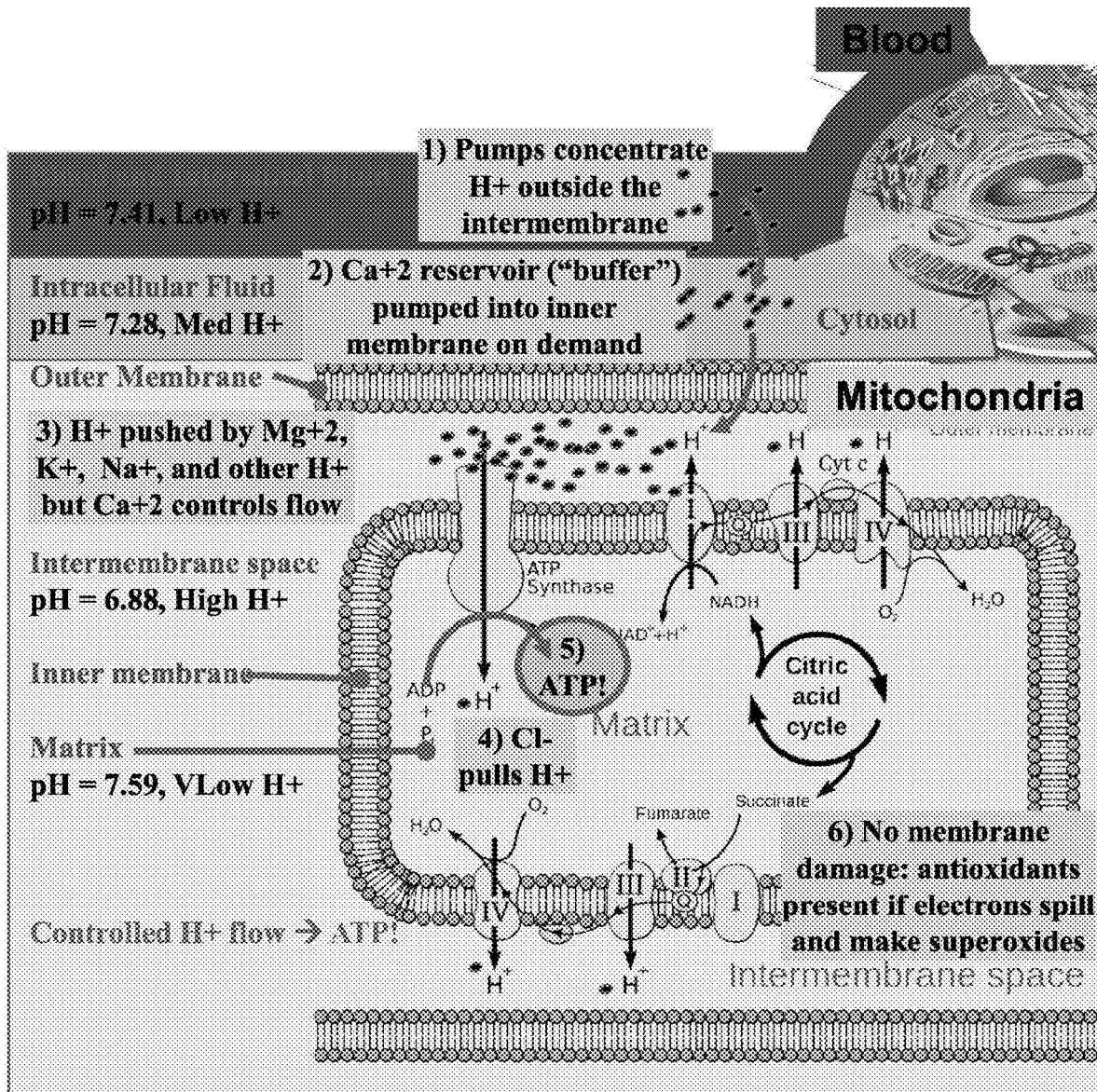
FIG. 1 depicts a diagram of the typical chemiosmotic gradient of hydrogen ions between the inner-membrane and matrix in a normally functioning mitochondria in a mammalian cell.

The present invention will now be described more fully hereinafter. However, many modifications and other embodiments of the present invention set forth herein, e.g., for the amelioration and/or treatment of specific conditions and disease states, will come to mind to one skilled in the art to which the invention pertains having the benefit of the teachings presented in the foregoing descriptions. Therefore, it is to be understood that the present invention is not to be limited to the specific embodiments disclosed and that modifications and other embodiments are intended to be included within the scope of the appended claims.

As used herein, the term "mammal" refers to humans as well as all other mammalian animals. As used herein, the term "mammal" includes a "subject" or "patient" and refers to a warm-blooded animal. It is understood that guinea pigs, dogs, cats, rats, mice, horses, goats, cattle, sheep, zoo animals, livestock, primates, and humans are all examples of animals within the scope of the meaning of the term. As used herein, "a mammal in need thereof" may be a subject who could have been, but is not required to have been, diagnosed as suffering from the condition intended to be treated. In one aspect, the present method is directed to conditions that are noticeable to the subject and the subject wishes to treat or ameliorate the condition without a formal diagnosis. Alternatively, a mammal in need thereof is one who has been diagnosed as having a condition and is in need of specific treatment. In other embodiments, a mammal may also be functioning normally relative to common standards but electively seeks to enhance performance for various purposes, such as for enhanced mental acuity or athletic interests.

The terms "subject" and "patient" are used interchangeably, and are meant to refer to any mammal, including humans, that has, or is at risk of developing, a dysfunctional cardiovascular condition. The subject or patient is typically human, however, other suitable subjects or patients include, but are not limited to, laboratory animals, such as mouse, rat, rabbit, or guinea pig, farm animals and domestic animals or pets. Non-human primates are also included.

As used herein, a "therapeutically effective amount" is an amount effective to elicit a cellular response that is clinically significant.

As used herein, the terms "treating" and "ameliorating" are intended to refer to all processes wherein there may be a slowing, interrupting, arresting, or stopping of the progression of the condition or symptoms, and does not necessarily indicate a total elimination of the underlying condition. The terms also encompass the administration of a pharmaceutical grade, physiological component, or natural physiological buffer composition wherein the mammal has a condition or symptom or a predisposition towards a condition or symptom, where the purpose is to cure, heal, alleviate, relieve, alter, improve or affect the condition or symptom or the predisposition to the same. Also contemplated is preventing the condition or symptom or the predisposition to the same, by prophylactically administering a pharmaceutical grade buffer composition as described herein.

As used herein, the term "pharmaceutical grade" means that certain specified biologically active and/or inactive components in the drug must be within certain specified absolute and/or relative concentration, purity and/or toxicity limits and/or that the components must exhibit certain activity levels, as measured by a given bioactivity assay. Further, a "pharmaceutical grade compound" includes any active or inactive drug, biologic or reagent, for which a chemical purity standard has been established by a recognized national or regional pharmacopeia (e.g., the U.S. Pharmacopeia (USP), British Pharmacopeia (BP), National Formulary (NF), European Pharmacopoeia (EP), Japanese Pharmacopeia (JP), etc.). Pharmaceutical grade further incorporates suitability for administration by means including topical, ocular, parenteral, nasal, pulmonary tract, mucosal, vaginal, rectal, intravenous and the like.

The present disclosure is based on the unexpected discovery that reducing physiological bloodstream pH in a subject is useful in treating, ameliorating, and preventing many conditions and diseases and symptoms thereof in a subject in need. The invention provides a stable therapeutic composition that can be administered to a subject in need thereof, in order to provide the requisite shift in blood pH.

FIG. 1 depicts a diagram of the chemiosmotic gradient potential of hydrogen ions in a normally functioning mitochondria in a mammalian cell. As shown therein, blood and interstitial fluid typically has a pH of around 7.4, the intracellular fluid within a cell has a pH of around 7.28, and intermembrane space of a mitochondria within the cell has a pH of around 6.88. Ionic pumps concentrate $H^+$ ions in the intermembrane space of the mitochondria, resulting in a large $H^+$ gradient between the intermembrane space and mitochondrial matrix across the inner membrane. The concentrations of other ionic species, such as $Ca^{2+}$, $Na^+$, $K^+$, $Mg^{2+}$, and $Cl^-$ are also manipulated to create an electrochemical gradient across the various membranes, and intramitochondrial $Ca^{2+}$ in particular is important for managing the flow of $H^+$ ions within the mitochondria. Hydrogen ions flow across the inner membrane into the mitochondrial matrix through ATP synthase, creating ATP from ADP. The electron transport chain is used to pump the $H^+$ ions back across the inner membrane to maintain the proton gradient. A small percentage of electron transfer occurs directly to oxygen, leading to free-radical formation, which contributes to oxidative stress and may result in membrane damage if insufficient antioxidants are present.

Figure 2:
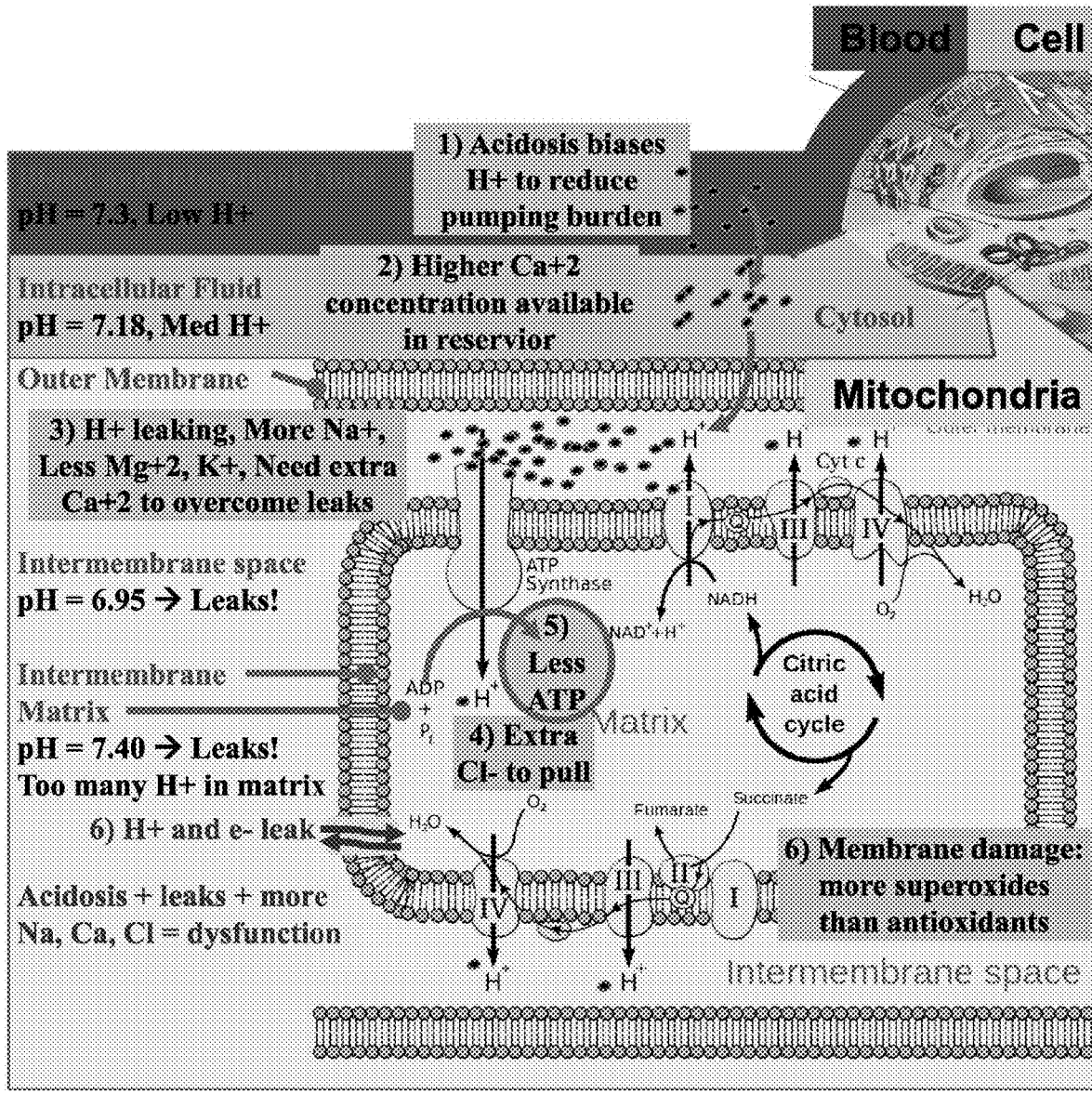
FIG. 2 depicts a diagram of the reduced chemiosmotic gradient of hydrogen ions in a mitochondria in a mammalian cell with a dysfunctional metabolism, as may occur after a prolonged exposure to a poor diet, or lack of exercise.

FIG. 2 depicts a diagram of the chemiosmotic gradient potential of hydrogen ions in a mitochondria in a mammalian cell with a dysfunctional metabolism, as may occur after a prolonged exposure to a poor diet, or lack of exercise. As shown in FIG. 2, the blood, interstitial space, and intracellular fluid have undergone acidotic shifts, i.e., increased the concentration of $H^+$ ions and reduced the pH. At the same time, the pH in the mitochondrial matrix is increased from normal due to membrane leaks or reduced H+ ion pumping action from the electron chain transport. As a result, the net $H^+$ electrochemical gradient available for the formation of ATP is reduced. Furthermore, the cell and mitochondria must increasingly rely on other ionic species to provide the necessary electrochemical gradient on demand, such as through higher than normal concentrations of $Ca^{2+}$ within the intermembrane space "pushing" hydrogen ions across the inner membrane and a higher concentration of $Cl^-$ within the mitochondrial matrix "pulling" the hydrogen ions. This dysfunctional ionic balance results in increased development of superoxidative species and increased membrane damage, and the metabolism of the cell slows down as a result. This reduces the amount of available ATP, causing a negatively reinforcing feedback loop that can lead to various adverse conditions and disorders.

A similar metabolic dysfunction occurs as a result of poor perfusion leading to a lactate burden, called metabolic acidosis in chronic state, which may be caused by, e.g., sepsis, multiple system atrophy (MSA), and ischemic conditions in peripheral limbs. For individuals incurring a chronic lactate burden, high blood levels of lactate steadily displace bicarbonate buffers to maintain acid-base homeostasis. A fraction of bicarbonate could then be removed by renal action to maintain homeostasis, and to reduce bloodstream bicarbonate levels. In addition, chronic disturbances in electrolytes can shift the setpoint for bicarbonate retention to additionally reduce stores. Such forces would in turn make less bicarbonate accessible for intracellular retention and intracellular buffering, ultimately reducing intracellular $H^+$ stores. This reduction in $H^+$ stores would require more $Ca^{2+}$ to sustain a desired chemiosmotic gradient, leading to a dysfunctional ionic balance as described above.

Stable therapeutic compositions of the present disclosure reduce the physiological bloodstream pH in a subject, and maintain that reduction in physiological bloodstream pH for a duration of time, until renal and respiratory compensation processes negate the reduction, commonly followed by an alkaline "rebound". The compositions of the present disclosure are formulated such that the formulated pH is below the physiologic norm (i.e., below 7.4). Bicarbonate concentration may, in some instances, be above physiologic norm (i.e., above 29 mM). The sudden influx of $H^+$ ions, together with excess bicarbonate, and the manipulation of the electrochemical gradients that results, allows for a return to normal mitochondrial metabolic processes, while other electrolyte, vitamin, and antioxidant support present in compositions of the present disclosure reduce the damage from oxidative stress. Other benefits of administration of compositions of the present disclosure include improvement of at least one of cardiovascular conditions, vasodilation, wound healing, vascular plaque, bicarbonate servicing, electrolyte economy, metabolic dysfunction, oxygen deficiency, Citric Acid Cycle, renal system operation, antioxidant dysfunction, angiogenesis, nitric oxide (NO) dysfunction, hormone function, and anemia.

In one embodiment of the invention, the compositions of the present invention are suitable for improvement of cardiovascular conditions, by reducing or removing vascular plaques. Plaque forms in the arteries as a result of a number of factors, which are rooted in a wound-related signal dysfunction, including for example, lipid dysfunction, nitric oxide dysfunction and excessive ROS, which are caused, in part, by the presence of an acidic environment in the cells. For example, in an acidic environment, exogenous ROS levels become elevated. Smooth muscle contains several sources of ROS, which have been shown to function as important signaling molecules in the cardiovascular system. The elevated ROS signals to the smooth muscles to accrue in the arteries, as though recruited to fill wounds that do not actually exist. Additionally, in an acidic environment with ROS and an absence of nitric oxide, macrophages are signaled to respond to a non-existent threat, causing them to convert from the M1 to the M2 form, and begin sequestering lipids. The fat laden lipids become accumulations of foam cells. Also, in acidic environment, an endothelial nitric oxide synthase (eNOS) dysfunction occurs, causing an increased availability of arginase, which is necessary for the synthesis of collagen, and thus works with acid-pH stimulated action of fibroblasts to promote an accrual of collagen in the arteries. The elevations of retained intracellular $Ca^{2+}$, and increases in unbound phosphate that occur from the metabolic dysfunction associated with an acidic environment (because less phosphate is complexed with ADP to form ATP), result in the promotion of calcific mineralized components of plaque. By restoring an alkaline environment in the cells, the compositions of the invention are able to reduce or reverse vascular plaque by correcting or improving at least one of, nitric oxide dysfunction (thereby restoring NO signaling), lipid dysfunction, eNOS dysfunction, reduction in smooth muscle recruiting, reduction of endogenous and exogenous reactive oxygen species (ROS), elevated $Ca^{2+}$, or restoration of fatty acid metabolism. For example, upon the introduction of an alkaline environment, the smooth muscles, in the absence of the ROS signal, recognize the absence of a wound, and consequently, they down-regulate, and begin to directionally orient towards their vasodilation and vasoconstriction tasks. Also, for example, in an alkaline, low ROS environment in the presence of eNOS nitric oxide signaling, foam cells are signaled to release their lipids. Along with the calcific plaque reversal or reduction, the suppleness of the vascular vessel returns. In addition, the acid-shifting action of the drug liberates atomic components of the mineral deposits, while magnesium in the composition of the invention aids in the prevention of plaque re-deposition, to reduce the hardening of the arteries from the mineral deposit components.

In one embodiment of the invention, the compositions of the present invention are suitable for preventing or minimizing hypoxia in a subject. The lack of sufficient oxygen reaching cells or tissues in a subject can occur even when blood flow is normal. This can cause many serious, sometimes life-threatening complications. Use of the compositions of the invention enable the resolution or improvement of conditions commonly associated with hypoxia, such as, for example, heart attack, cardiovascular problems, lung conditions, concussive cascade, reperfusion injury, myocardial infarction, hypoxia associated with diabetes, tissue trauma, and the like. Many of these conditions are associated with vasoconstriction. The composition can counteract such vasoconstriction by promoting vasodilation via at least one of three pathways, namely endothelin, prostacyclin, or NO-soluble guanylyl cyclase (NO-sGC). For the endothelin pathway, the compositions elevate $Mg^{2+}$ in the bloodstream to antagonize $Ca^{2+}$. This blocks $Ca^{2+}$ from potentiating vasoconstriction, allowing the arteries to relax and dilate. Meanwhile, the compositions also provide metabolic corrections to reduce metabolic sources of ROS, and reduce the presentation of endothelin stimulants at the cell surface, thereby reversing $Ca^{2+}$ overstimulation. For the prostacyclin pathway, niacinamide in the composition elevates adenosine 3',5'-cyclic monophosphate (cAMP) activity, which completes prostacyclin potentiation towards vasodilation. For the NO-sGC pathway, as noted above, the compositions of the invention provide a gradient of $H^+$ flowing into the cells to promote $Ca^{2+}$ efflux, which corrects elevated $Ca^{2+}$ presentation. One effect of high levels of $Ca^{2+}$ is the elevation of caveolin. As the caveolin elevate, they take residence in the caveoli on the cell surface, causing the displacement of eNOS, which migrates to the Golgi system. The combination of low ROS and low intracellular $Ca^{2+}$ achievable using the composition of the invention, allows eNOS, to return from the Golgi to the cell membrane, thereby to restoring eNOS's ability to promote vasodilation. As the eNOS returns to the membrane, the bloodstream pH shifts, promoting NO release via the NO-sGC pathway, and promoting vasodilation. In addition, renal responses to rebalance pH produce a second "pH shift" towards alkaline, once again stimulating NO/NO-sGC vasodilation to extend the duration of the effect.

Figure 3:
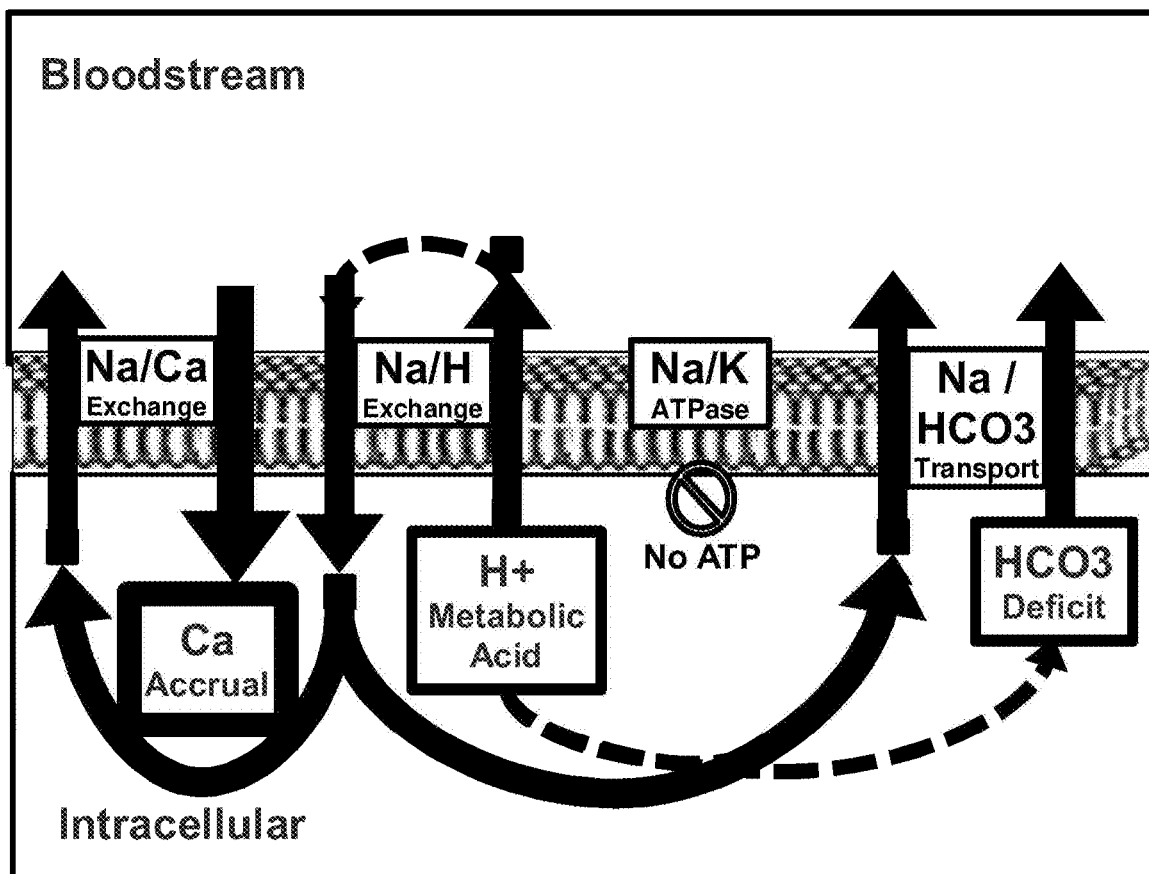
FIG. 3 depicts a diagram of the chemiosmotic flow of ions into and out of the cell of a subject having a hypoxic crisis, or as observed in phases of acid-base disturbance, such as during or following exercise, or as observed during or following use of the composition of the invention.
Figure 4:
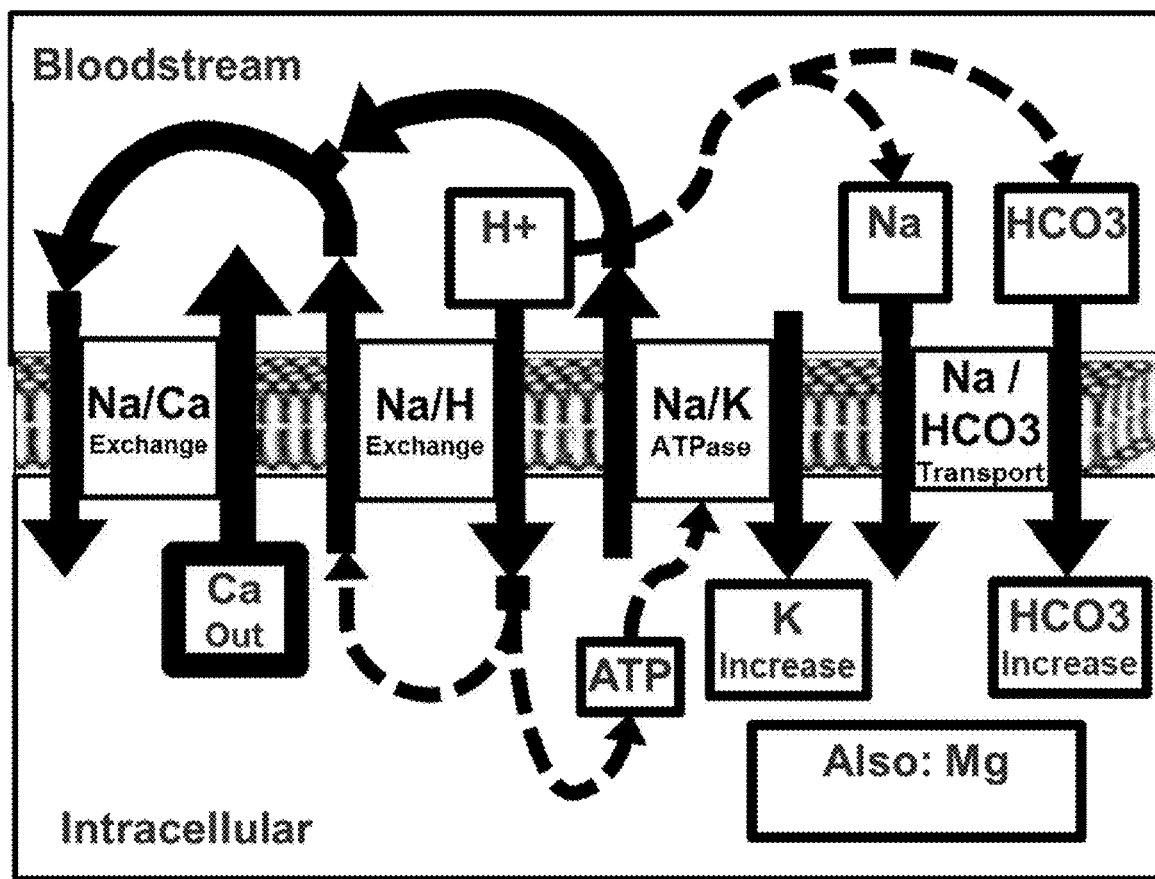
FIG. 4 depicts a diagram of the chemiosmotic flow of ions into and out of the cell of a subject having had the hypoxic crisis corrected by use of the composition of the invention.

As shown in FIG. 3, when a subject's body is under a state of metabolic crisis, such as a hypoxic crisis, intracellular acidification drives the intracellular accrual of $Ca^{2+}$. This occurs because adenosine triphosphate (ATP) is required to resolve the sodium burden created as $H^+$ leaves the cell. However, in the hypoxic state, ATP becomes impaired, and as a consequence, the $Na^+/K^+$ ATPase pump becomes inactive. The $Ca^{2+}/Na^+$ exchange must resolve the $Na^+$ burden by accumulating $Ca^{2+}$ in the cell. To reverse this process, the hypoxic state must be resolved to restore ATP production (and $Na^+/K^+$ ATPase), or extracellular $H^+$ must be presented. As shown in FIG. 4, the compositions of the invention achieve both of these things, enabling the rapid resolution of the $Ca^{2+}$ overburden and the corresponding metabolic crisis. The composition adjusts the pH of the bloodstream, acidifying it, and in doing so, causes $H^+$ to enter through the $Na^+/H^+$ exchange route. As the $H^+$ enters, it pushes $Na^+$ out. As noted above, the composition of the invention promotes vessel vasodilation to improve blood flow. With this increased blood flow comes increased oxygen, entering, which enables the creation of ATP through aerobic metabolism. The composition also elevates $Mg^{2+}$ in the bloodstream. The increased $Mg^{2+}$ facilitates the transport of the ATP, as Mg-ATP, to the $Na^+/K^+$ ATPase, providing the stimulus to push $Na^+$ out. Some of the increased $Na^+$ in the bloodstream reenters through the $Ca^{2+}/Na^+$ exchange. Additionally, the bloodstream presentation of $H^+$, in concert with elevated bloodstream bicarbonate, promotes bicarbonate entry into the cell. This process provides an antidote to reverse calcium accrual in the cell, improving the cells' capacity to restore a chemiosmotic gradient with less reliance on $Ca^{2+}$ and more utility of $HCO3-$ buffered $H^+$ to ultimately reduce metabolic acid burden and metabolic ROS, to promote restoration of the intracellular towards alkaline, with improved redox status. The steady biasing towards alkaline and low ROS promotes positive rebalancing of electrolytes and pH in the cytosol, organelles, lysosomes, peroxisomes, calcium status, magnesium status and ROS status within the cell. Additionally, it changes the cellular economy to restore potassium and bicarbonate, while at the same time reducing intracellular calcium.

The vasodilation that can be achieved by use of the composition of the invention makes the composition useful for wound care. It was unexpectedly discovered that use of the compositions of the invention may provide wound recovery even in subjects who have exhausted conventional treatment methods, including those with gangrenous presentation, or chronic, diabetic or traumatic wounds. Metabolic changes are among the effects observed following trauma injury and surgical trauma. These include inflammatory responses, which trigger a constriction of blood flow to the affected regions. While this advantageously minimizes blood loss at the site of an open wound or internal bleed, it may impair healing by promoting a hypoxic intracellular environment. In trauma situations where bleeding risk is absent or reduced (for example by compression), it may be desired to suppress the inflammatory response, to avoid secondary injuries from hypoxia. In cases of chronic inflammation, such as with chronic critical limb ischemia (CLI), the suppression of inflammation can expedite healing. The vasodilation promotion and improved perfusion caused by the composition of the invention contribute towards breaking the cycle of inflammation. In addition to promoting vasodilation in order to increase oxygen servicing, the compositions of the invention are also capable of correcting key metabolic aberrancies that are present in wounds. The compositions may, for example improve at least one of restoring acid-buffer status and correction of elevated $Ca^{2+}$; reducing metabolic sourced ROS; correcting acidosis; correcting over-active iNOS and restoration of eNOS and nNOS function; promotion of beneficial angiogenesis after eNOS is corrected; and suppression of iNOS promoted aberrant angiogenesis, all of which are important for wound care.

Because $H^+$ also administrates acetylcholine uptake, which is part of muscle support, and is a part of the cerebellum control process, and ATP is relevant for all of these systems, disorders of the central nervous system are another treatment target. Additionally, action to resolve intracellular acid, calcium accrual, reduced ROS, and increased Mg, are factors that can enhance function in the peroxisome, to better maintain catalase antioxidant supply, and additionally support the lipid modeling required for myelin maintenance of nerve sheaths.

In some instances, the reduction in physiologic bloodstream pH caused by the composition of the invention may be minimal, or not observed, due to the particular formulation of an administered composition, the rate at which a composition is administered, or both. However, the therapeutic benefits described herein may still be achieved due to the net elevation of bicarbonate concentration that occurs. Due to an excess of $H^+$ upon administration, the body prioritizes retention of, and augmentation of, the buffer components (e.g., bicarbonate), as acid balancing processes proceed. Thus, a greater fraction of the buffering agent is retained within the cells and bloodstream as the system alkalinizes and returns the physiological pH towards baseline. Such an "alkaline rebound" may result in bloodstream pH overshooting slightly for a net alkaline stabilization relative to the starting pH. The "alkaline rebound' achieves a higher residual concentration of intercellular and bloodstream buffer components, including bicarbonate. Alternatively, the system may regulate to a final pH equivalent to that present prior to treatment, but with bloodstream buffering, with regard to acidic species, being increased. Alternately, the bloodstream pH may settle to be more acidic than prior to the treatment, yet while a variety of aforementioned exchange phenomena are promoted. In contrast to infusion of a simple buffer, such as bicarbonate, in the absence of acidic components, co-administration of acid and buffer are key to limiting the $H^+$ efflux rate, while the intracellular calcium correction is achieved.

In one embodiment of the invention, the compositions of the present invention are suitable for increasing nitric oxide synthase (NOS) in a subject. The pH biasing and increase in bicarbonate concentration as provided by compositions of the present disclosure (including decreases in pH upon administration and "alkaline rebounds" as homeostasis is restored) may also restore endothelial and neuronal NOS, leading to a selective increase in nitric oxide production. Nitric oxide is a gaseous signaling molecule with a role in, e.g., hemostasis, smooth muscle (particularly surrounding vasculature), neuronal signaling, and in the gastrointestinal tract. NO has been implicated in a variety of physiological systems, and the increased levels resulting from administration of the compositions described herein may serve a role in providing the therapeutic benefits described herein. For example, in glaucoma, NO may play a role in regulating intraocular pressure via the trabecular meshwork. In atherosclerotic plaques, NO stops the aberrant perpetuation of smooth muscle recruitment, foam cell accrual and lipid storage, and collagen deposition, and it may ultimately lead to reversal of plaque damage and a return of the vascular section to physiological norms.

In one embodiment of the invention, the compositions of the present invention are suitable for reducing lactate burden in a subject in need thereof. As used herein, the term "lactate burden" means any physiological condition characterized by elevated lactate levels. This may include, for example and without limitation, chronic lactate burdens such as acidosis, sepsis, and MSA, or acute lactate burdens such as may occur during and after physical exertion such as exercise. Lactate circulating oxygen debt burden that is retained in muscles, can be stimulated to be released by bicarbonate, and subsequently metabolized thus lowering the subject's lactate burden. The ability to eliminate lactate burden is important for a subject who has had, for example, an organ transplant. Where the transplant procedure involves the use of citrate anticoagulant, the citrate must be metabolized. This metabolization can induce a lactate burden in those individuals. Additionally, lactate burden is a component of sepsis and a chronic burden in diabetics. In the above instances, as well as in others involving a lactate burden, the use of the compositions of the invention may reduce that burden.

In one embodiment of the invention, the compositions of the present invention are suitable for reducing acidosis in a subject in need thereof, by administering to the subject the composition of the invention. One of the metabolic effects of trauma is the suppression of insulin, resulting in a reduction of the normal anabolic effect of insulin towards an increase in catabolic effects. This leads to a shift towards free fatty acids as the primary source of energy, with triglycerides providing 50 to 80% of the energetic need. Reducing the catabolic response encourages faster healing after surgery. These same mechanisms are in play in the diabetic patient, and become a larger challenge as subjects progress in their metabolic dysfunction. Underlying this catabolic process are aberrations in the metabolic chain that tend towards incomplete oxidation, leading to an increase in acidic products and an elevation of ROS from metabolic sources. As noted herein above, in trauma, this catabolic shift is driven by the hypoxic state, as inflammation and the vasoconstrictive response impair circulation. In diabetes, the shift is marked by glucose intolerance, and compounded by plaque-induced circulatory impairments and a sedentary lifestyle. In both cases, incomplete oxidation results in acidification in the cell and the promotion of transport biases which cause $Ca^{2+}$ to concentrate in the cytosol. This concentration of $Ca^{2+}$ cascades to the mitochondrial inner-membrane so that $Ca^{2+}$ takes on a larger role in the chemiosmotic gradient, reducing the role of $H^+$ itself. Such a shift in $Ca^{2+}$ and $H^+$ initiates a progressive shutdown in the electron chain transport (ECT), so that $Ca^{2+}$ takes on a greater role in controlling the chemiosmotic potential. This also leads to an increase in metabolic ROS from ECT stages. Over time, impaired circulation reduces B-vitamin servicing, which impairs both the Krebs cycle and ECT, further increasing metabolic ROS. At the same time, impaired circulatory servicing reduces antioxidant maintenance to leave the elevation in ROS unchecked. While such aberrations have beneficial qualities, such as promoting the creation of NAPDH oxidases for bactericidal function during infection, they also present impairment to the healing process, as they promote catabolism. Furthermore, a balance of signals including acidosis, hypoxia, $Ca^{2+}$, ROS and iNOS/NO, collectively suppress emergence of M2 macrophages, as desired, to promote healing. To address these aberrancies, the composition of the invention facilitates $Ca^{2+}$ correction, and enhances B-vitamin servicing and ascorbic acid anti-oxidant servicing via elevated presentation. Additionally, acid burden is reduced, promoting an alkaline bias. Elevated $HCO_3^-$ buffer levels also serve to preserve this alkaline bias.

The elements of metabolism referenced above also affect insulin management. For example, insulin release is stimulated from the pancreas when a signal of elevated $Ca^{2+}$ is released to the bloodstream. For $Ca^{2+}$ to be released to the pancreas, hydrogens must be created, through incomplete metabolism, to displace $Ca^{2+}$ from the cytosol to the bloodstream. As noted herein-above, the $Na^+/K^+$ ATPase must be served with $Mg^{2+}$ and ATP to facilitate the flooding Na to the bloodstream to ultimately stimulate the $Na+/Ca^{2+}$ exchanger to release $Ca^{2+}$ to the bloodstream. Additionally, for sensing of elevation to occur, the background level of $Ca^{2+}$ in the bloodstream needs to be low enough for the pancreas to observe the change. In acidosis, this would be impaired as $Ca^{2+}$ solubility is elevated in the blood and in the cytosol. As a further example, ROS, such as peroxide, can promote insulin function, when presented at low levels, and prevent presentation and action of insulin when presented at high levels. Thus, correction of acidosis and enhancement of $Mg^{2+}$ are key to restore insulin management. So too are suppression of ROS (e.g., $H_2O_2$) through antioxidant support and facilitation of TCA and ECT function to achieve near-complete oxidation of Acetyl-CoA to $CO_2$ and $H_2O$.

Compositions

In one embodiment of the invention, the composition of the invention is a stable therapeutic composition that has been formulated to make it suitable for intravenous administration to a subject. The composition contains an intravenous buffer solution, containing at least one pharmaceutical grade acid, and at least one pharmaceutical grade pH buffering agent. To ensure their suitability for pharmaceutical use, the acid and buffer solution are present in a sterile aqueous solution. The concentration of the pharmaceutical grade acid and the pharmaceutical grade pH buffering agent in the buffer solution is sufficient to provide a total titratable acid content of from 60 mmol/L to 3000 mmol/L when administered to a subject. The acid and base are selected so that they are able together, to provide a buffer solution having a pH of between 4 and 7.7.

In one embodiment of the invention, the concentration of the pharmaceutical grade acid and the pharmaceutical grade pH buffering agent in the buffer solution is sufficient to provide a total titratable acid content of from 80 mmol/L to 3000 mmol/L when administered to a subject, where the buffer solution is effective to provide a buffer solution pH of less than 5.5. In another embodiment of the invention, the concentration of the pharmaceutical grade acid and the pharmaceutical grade pH buffering agent in the buffer solution is sufficient to provide a total titratable acid content of from 100 mmol/L to 2000 mmol/L when administered to a subject, where the buffer solution is effective to provide a buffer solution pH of less than 5.5. embodiment of the invention, the concentration of the pharmaceutical grade acid and the pharmaceutical grade pH buffering agent in the buffer solution is sufficient to provide a total titratable acid content of from 200 mmol/L to 1000 mmol/L when administered to a subject, where the buffer solution is effective to provide a buffer solution pH of less than 5.5.

In one embodiment of the invention, the concentration of the pharmaceutical grade acid and the pharmaceutical grade pH buffering agent in the buffer solution is sufficient to provide a total titratable acid content of from 40 mmol/L to 3000 mmol/L when administered to a subject, where the buffer solution is effective to provide a buffer solution pH of less than greater than or equal to 5.5. In another embodiment of the invention, the concentration of the pharmaceutical grade acid and the pharmaceutical grade pH buffering agent in the buffer solution is sufficient to provide a total titratable acid content of from 60 mmol/L to 2000 mmol/L when administered to a subject, where the buffer solution is effective to provide a buffer solution pH of less than greater than or equal to 5.5. embodiment of the invention, the concentration of the pharmaceutical grade acid and the pharmaceutical grade pH buffering agent in the buffer solution is sufficient to provide a total titratable acid content of from 80 mmol/L to 3000 mmol/L when administered to a subject, where the buffer solution is effective to provide a buffer solution pH of less than greater than or equal to 5.5.

An acid is a molecule or ion that is capable of donating a hydrogen ion $H^+$. The amount of $H^+$ ions in a solution is measured by its pH, where a pH of less than 7 constitutes an acidic pH. Humans typically have a bloodstream pH of 7.4. Compositions of the present disclosure comprise an acid that provides an amount of $H^+$ ions to decrease the physiological bloodstream pH in a subject. Without being bound to any theory, it is believed compositions of the present disclosure increase the $H^+$ gradient in various cellular environments, including, e.g., mitochondria. This increased mitochondrial $H^+$ gradient drives higher production of ATP and, through other physiological homeostatic systems, causes changes in concentration gradients of the cellular membranes which in turn rebalances physiological ions such as sodium, magnesium, potassium, and calcium. For example, an increased $H^+$ gradient in the bloodstream may stimulate calcium pumps in cellular membranes, thereby increasing intracellular $H^+$ and reducing intracellular $Ca^{2+}$. The concentration gradients of sodium, magnesium, and potassium are also affected. By manipulating ionic gradients using compositions of the present disclosure, many conditions and diseases and symptoms thereof may be treated, ameliorated, or prevented.

In some embodiments, compositions of the present disclosure are sufficient to reduce the bloodstream pH of a subject by a small, moderate, or large amount. In some embodiments, the amount of acid in a composition of the present disclosure is sufficient to reduce the bloodstream pH of a subject by 0.01, 0.02, 0.03, 0.04, 0.05, 0.06, 0.07, 0.08, 0.09, 0.1, 0.15, 0.2, 0.3, 0.4, 0.5, 0.6, 0.7, 0.8, 0.9, 1.0, or 1.1, or more. The reduction in pH may also be expressed by the desired pH level of the bloodstream after administration of a composition of the present disclosure, e.g., 7.2. In some embodiments, a composition of the present disclosure comprises sufficient acid to reduce the bloodstream pH of a subject to 7.3, 7.2, 7.1, 7.0, 6.9, 6.8, 6.7, 6.6, 6.5, 6.4, or 6.3. A reduction of bloodstream pH to below 6.3 is not typically advised, as it may pose a cell health risk and threaten the integrity of cellular phospholipid bilayers. In cases of alkalosis where nominal pH may exceed 7.4, a "reduction" in pH provided by administration may still result in a bloodstream pH exceeding 7.4. For example, administration of a composition of the present disclosure may shift the physiological pH from 7.7 to 7.5.

Compositions of the present disclosure may contain one or more pharmaceutical grade acids. In some embodiments, compositions of the present disclosure comprise a mixture of one or more pharmaceutical grade acids. Acids may include any physiological acceptable acid, including, without limitation, hydrochloric acid, ascorbic acid, citric acid, lactic acid, phosphoric acid, or combinations thereof. The pH of a composition of the present disclosure may be between about 4 and 7.7. In some embodiments, the pH of a composition of the present disclosure is between about 6.1. In embodiments where the pH of the composition is very low, the rate of administration may have to be managed to avoid tissue damage adjacent to the injection site as dilution is effected in the bloodstream.

In another aspect, compositions of the present disclosure comprise a pH buffering agent. A pH buffering agent is a weak acid or base that is used to maintain the pH of a solution near a desired value. Compositions of the present disclosure comprise a pH buffering agent such that the reduction in bloodstream pH may be sustained for a desired duration. In some embodiments, the pH buffering agent may comprise a conjugate acid or a conjugate base. In some embodiments, the pH buffering agent may comprise any physiological acceptable buffering agent, including, without limitation, sodium bicarbonate, a phosphate buffer, citrate buffer, or a synthetic buffer creating specific alkaline conditions (e.g., tris-hydroxymethyl amino methane), or combinations thereof.

The buffer capacity of a solution is a measure of the solution's ability to resist pH change, i.e., to maintain a specific pH level. As discussed above, acid-base homeostasis relates to the proper balance of acids and bases in extracellular fluids, i.e., the pH of the extracellular fluid. In humans, the pH of plasma is approximately 7.4 and is tightly maintained around that value by three interconnected systems: 1) buffering agents, including bicarbonate, phosphate, and proteins), 2) the respiratory system, which impacts the partial pressure of carbon dioxide in blood plasma, and 3) the renal system, which excretes waste acids and bases. Accordingly, in some embodiments, compositions of the present disclosure comprise a pH buffering agent in order to maintain the desired bloodstream pH level below the typical pH value of about 7.4 in the face of pressures exerted by the physiological systems that regulate acid-base homeostasis. In some embodiments, compositions of the present disclosure comprise a pH buffering agent in an amount sufficient to maintain the reduction in bloodstream pH, or to maintain the desired pH level, for a duration of 1 minute to 1 week.

The desired duration of the reduced bloodstream pH level will depend on the particular indication being treated as well as the individual being treated. In some embodiments, a small, moderate, or large buffer capacity may be desired. In one means of administration, a small quantity of drug and/or a slow administration of a drug product could stimulate compensatory processes that can be respiratory or renal, so as to mitigate observable acid shifting potential, but having stimulated respiratory and renal activity. In such cases, a blood stream response may be neutral or may tend toward alkaline. Alternatively, administration of a high dose, and/or a dose with a fast administration rate, such as a bolus or fast IV drip could introduce the acid and overwhelm the compensatory processes to yield an observable downstream pH toward acidic. Such a stimulus would commonly be expected to be followed by a rebound of bloodstream pH towards alkaline throughout the treatment or post-treatment. The outcome resulting from a given dose level and/or administration rate may be different from patient to patient and from administration to administration as the patient's health, electrolytic status, pH status and compensatory process status evolve. Different buffer capacities may be sufficient to maintain the reduction in bloodstream pH for a duration of 1 minute to 1 week. In other embodiments, the buffer capacity may also be expressed in molar equivalent of common buffers, such as bicarbonate.

In some embodiments, the composition has a buffer capacity between 0.1 mM $HCO_3^-$ equivalent and 1200 mM $HCO_3^-$ equivalent. In other embodiments, the buffer capacity is between 0.1 mM $HCO_3^-$ equivalent and 10 mM $HCO_3^-$ equivalent. In some embodiments, the buffer capacity is between 10 mM $HCO_3^-$ equivalent and 50 mM $HCO_3^-$ equivalent. In some embodiments, the buffer capacity is between 10 mM $HCO_3^-$ equivalent and 1000 mM $HCO_3^-$ equivalent. In some embodiments, the buffer capacity is between 50 mM $HCO_3^-$ equivalent and 800 mM $HCO_3^-$ equivalent. In some embodiments, the buffer capacity is between 100 mM $HCO_3^-$ equivalent and 600 mM $HCO_3^-$ equivalent. In some embodiments, the buffer capacity is between 200 mM $HCO_3^-$ equivalent and 550 mM $HCO_3^-$ equivalent. In some embodiments, the buffer capacity is between 20 mM $HCO_3^-$ equivalent and 100 mM $HCO_3^-$ equivalent. In other embodiments, buffer capacity may be expressed by the molar concentration of $HCO_3^-$, or other common buffers. For example, in some embodiments, the molar concentration of $HCO_3^-$ may be between 0.01 molar and 10 M. In other embodiments, the molar concentration of $HCO_3^-$ may be between 0.5 and 2 M.

In another embodiment, the present disclosure provides a composition having a pH below physiological pH (i.e., below 7.4) and an $HCO_3^-$ concentration above physiological levels (i.e., above 29 mM). In some embodiments, the pH of the composition may be between 4 and 7.7 and the $HCO_3^-$ concentration may be between 30 mM and 2 M). In other embodiments, the pH of the composition may be between 5.5 and 7.4. In further embodiments, the pH of the composition may be around 6.

Figure 5:
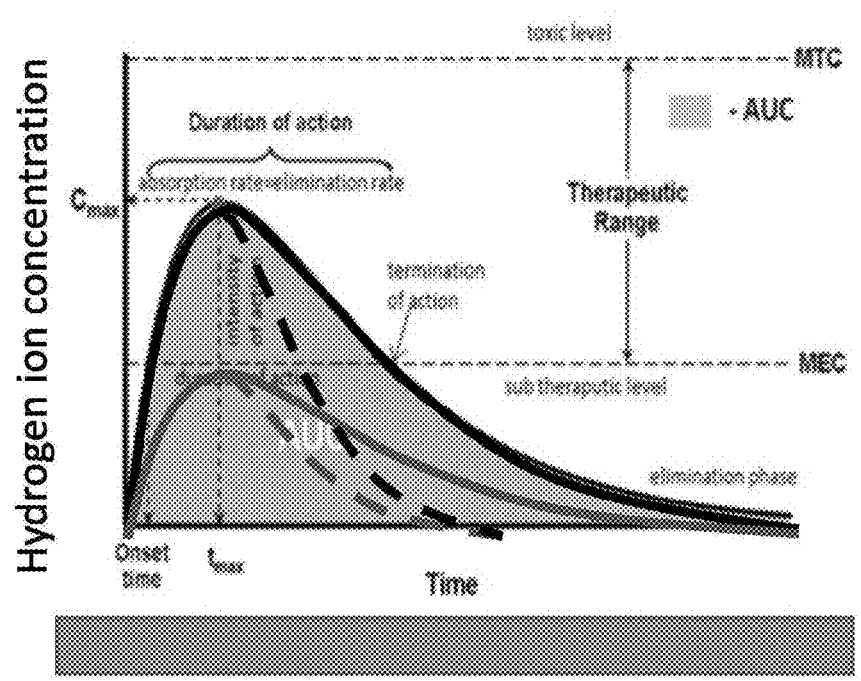
FIG. 5 shows a diagram of the amplitude and duration of an acid state shift caused by different formulations of compositions of the present disclosure.

FIG. 5 shows a diagram of the amplitude and duration of an acid state shift caused by different formulations of compositions of the present disclosure. The black lines, both solid and dotted, depict a large acid shift, i.e., a composition with a high concentration of $H^+$ ions. However, the buffering capacity of the composition depicted by the dotted black line is smaller than that of the solid line, such that the acid shift is maintained for a shorter duration. The gray lines, both solid and dotted, depict a smaller acid shift, i.e., a composition with a lower concentration of $H^+$ ions. Again, the buffer capacity between these compositions varies such that the acid shift caused by the composition depicted by the dotted gray line is maintained for a shorter duration. Compositions of the present disclosure may be designed along these two spectrums, amplitude of shift and duration of shift, according to desired therapeutic properties and administration schedules.

In another embodiment, the present disclosure provides a stable therapeutic composition comprising a buffer solution comprising a pharmaceutical grade base and at least one pharmaceutical grade conjugate acid, wherein the buffer solution is sufficient to raise the physiological bloodstream pH of a subject by 0.1 to 1.1, and wherein the buffer solution has a buffer capacity sufficient to sustain the elevation of the physiological bloodstream pH. In some embodiments the buffer capacity may be sustained for a period of time for example 1 minute or 1 week. The compositions may further comprise vitamins, salts, acids, amino acids or salts thereof, and stabilized oxidative species.

In another aspect, compositions of the present disclosure may further comprise salts to provide sources of physiological relevant ionic species, such as $Na^+$, $K^+$, $Mg^{2+}$, $Cl^-$, $PO_4^{3-}$, or $Ca^{2+}$. These may include, without limitation, sodium chloride, disodium phosphate, potassium chloride, monopotassium phosphate, magnesium chloride, and calcium chloride. The compositions may further comprise other trace elements and their salts, including, but not limited to, selenium, copper, chromium, iodine, fluoride, zinc, manganese, molybdenum, and iron.

Sodium ions are required in relatively large concentrations for normal physiological functioning. It is the major cation of the extracellular fluid. It plays an important role in many physiological processes, including the regulation of blood volume, blood pressure, osmotic equilibrium, and pH, as well as the generation of nerve impulses.

Potassium ions are the major cation of intracellular fluid, and, with the sodium ions of the extracellular fluid, is a primary generator of the electrical potential across cellular membranes. Accordingly, it plays a significant role in normal functioning, and is critical in such body functions as neurotransmission, muscle contraction, and heart function.

Calcium ions are likewise important to many physiological processes. In particular, $Ca^{2+}$ ions are one of the most widespread second messengers used in signal transduction. In endothelial cells, $Ca^{2+}$ ions may regulate several signaling pathways which cause smooth muscles surrounding blood vessels to relax. Dysfunction within $Ca^{2+}$-activated pathways can lead to an increase in tone caused by unregulated smooth muscle contraction. This type of dysfunction can be seen in cardiovascular diseases, hypertension, and diabetes.

Magnesium ions are required in relatively large concentrations in normal metabolism. It is recognized that deficiency of magnesium is rare unless it is accompanied by severe losses in other electrolytes such as in vomiting and diarrhea. It is however frequently recognized as deficient in the modern diet with symptoms such as muscle tremors and weakness. This mineral is important in many enzymatic reactions and will stabilize excitable membranes. Administered intravenously, magnesium may produce an anesthetic action and this is indirect evidence of its action on the vascular wall endothelial component to stabilize and normalize the surface of the vascular wall.

In some embodiments, a composition of the present disclosure comprises $Na^+$ at a concentration between 0.1 mM and 1 M. In other embodiments, a composition of the present disclosure comprises $K^+$ at a concentration between 0.0 mM and 1 M. In some embodiments, a composition of the present disclosure comprises $Mg^{2+}$ at a concentration between 0.1 mM and 1 M. In other embodiments, a composition of the present disclosure comprises $Ca^{2+}$ at a concentration between 0.1 mM and 1 M.

As described above, the interplay between the various ionic species is disrupted in various physiological conditions, and compositions of the present disclosure may include these species to aid in the restoration of normal physiological conditions and concentrations. For example, high intracellular $Ca^{2+}$ may be restored to a lower level as offset by $Mg^{2+}$, $K^+$, and $H^+$, which may lead to NOS presentation in the cytosol and restoration of NO levels.

As stated above, the compositions described herein may include vitamins and vitamers, which is a substance(s) that has vitamin-like activity. Vitamins selected from the group consisting of the water soluble and lipid soluble group, and a combination of two or more thereof may also be added to the pharmaceutical composition. Preferably, the pharmaceutical composition includes ascorbic acid. Ascorbic acid is included as a strong antioxidant component and to maintain the structural integrity of connective tissue, including epithelial basement membranes and to promote wound healing. It may also play a distinct role as an agent with strong anti-inflammatory actions. The oxidized form of the vitamin, dehydroascorbic acid, has been shown to transfer intracellularly where some of it is reduced within the cell via action of glutathione. Deficiencies of other B group and A and E are also protected by ascorbic acid and corresponding interactions of dehydroascorbic acid and glutathione. In some embodiments, a composition of the present disclosure comprises dehydroascorbic acid, an oxidized form of ascorbic acid that is actively imported into the endoplasmic reticulum of cells via glucose transporters. Presentation of dehydroascorbic acid can also stimulate production of glutathione in the liver, which facilitates recycling of dehydroascorbic acid into ascorbic acid. Thus, dihydro-ascorbic acid indirectly enhances intracellular antioxidant resources. Dehydroascorbic acid may be present via direct inclusion of pharmaceutical grade dehydroascorbic acid, or by conversion of ascorbic acid via contact with a reactive oxygen species such as $HOCl$, $H_2O_2$, or $OCl$.

The B Group of Vitamins has been shown to be important in human food intake, and plays an important role acting as co-enzymes in cellular metabolism and energy production. The entire B group of vitamins may be included in the formulation to address any deficiencies in the patient population to be treated.

The B group vitamins are found to occur naturally together in foods and are generally included comprehensively for this reason. The B group includes: 1) Thiamine (B1), which plays an important role in energy production within the cell, specifically as co-enzyme in metabolism of carbohydrates. At least 24 enzymes are known to use thiamine as a co-enzyme; 2) Riboflavin (B2) in the form of flavin mononucleotide and flavin adenine dinucleotide are part of all dehydrogenase enzymes. Deficiency of this vitamin causes inflammation of the mouth, tongue, dermatitis, defective vision and blood dyscrasias; 3) Niacinamide (B3) is included, as part of the B group of vitamins as deficiency syndromes in clinical pellagra are well known clinical manifestations of deficiencies. The deficiency states of this vitamin are associated with intestinal diseases and alcohol misuse. It also occurs in diabetes mellitus and carcinoid syndrome. The active forms of this vitamin include the nicotinamide dinucleotides NAD and NADP, which are the co-enzymes and co-substrates for numerous dehydrogenases responsible for oxidation-reduction systems within the human cell, which are indispensable for energy production.

The formation of nicotinic acid from the administered nicotinamide in the formulation produce nicotinic acid possessing additional actions not shared by nicotinamide, such as inhibition of cholesterol synthesis; 4) Calcium D-Pantothenate (B5), pantothenic acid forms a major part of the molecule of co-enzyme A, which is important in the energy producing metabolic cycles in the mitochondria of all cells. The effect of this vitamin on various disease syndromes has been recognized. Such as its use in neurotoxicity produced by streptomycin and it's use in diabetic neuropathy, skin diseases and adynamic ileus; and 5) Pyridoxine (B6) is widely utilized as a co-enzyme in over 40 types of enzymatic reactions. The B Group of vitamins may also aid in providing an increase of antioxidants and stimulated glutathione to reduce reactive oxygen species, which ultimately aids in NO expression.

The most important of these are the transamination reactions and the influence of pyridoxine on tryptophan metabolism. Kynureminase, which is an enzyme used to identify pyridoxine deficiencies, loses its activity when pyridoxine is not present and may result in secondary nicotinic acid deficiency as a result of lack of the kynureminase conversion of nicotinic acid from tryptophan.

Cyanocobalamin (B12) is used because of the frequent reports of mal-absorption of cyanocobalamin, caused by poor dietary habits, senescence, and certain drugs (metformin) used as a hypoglycemic agent in diabetes mellitus. This vitamin is essential for normal erythropoiesis to occur, and recent findings have also implicated this vitamin with improvement of neuronal transmission in motor neuron disease. (Rosenfeld, Jeffrey and Ellis, Amy, 2008, Nutrition and Dietary Supplements in Motor Neuron Disease, *Phys Med Rehabil Clin N Am.,* 19(3):573-589).

Vitamin K is a fat-soluble vitamin. There are two naturally occurring forms of the vitamin. Vitamin K1 is the dietary Vitamin K and is abundant in green leafy vegetables, whereas vitamin K2 is present in tissues. Vitamin K2 is synthesized by bacteria. It is found mainly in fermented products like fermented soybeans, cheese, curds and to some extent also in meat and meat products (Thijssen, H. H., M. J. Drittij-Reijnders, and M. A. Fischer, 1996, Phylloquinone and menaquinone-4 distribution in rats: synthesis rather than uptake determines menaquinone-4 organ concentrations, *J Nutr* 126:537-43). Vitamin K2 is found in animals as menaquinone. It is the human activated form of vitamin K and is said to promote the healing of bone fractures. It is essential for the carboxylation of glutamate residues in many calcium binding proteins such as calbindin and osteocalcin. These proteins are involved in calcium uptake and bone mineralization.

There is an established daily dosage for vitamin K1 for, but not for vitamin K2. A typical therapeutic oral dose for vitamin K2 for osteoporosis is 45 mg/day. Unlike for coagulation, a much higher level of vitamin K is needed for complete gamma-carboxylation of osteocalcin (Booth, S. L., and J. W. Suttie, 1998, Dietary intake and adequacy of vitamin K, *J. Nutr* 128:785-8). Vitamin K deficiency is associated with reduced hip bone mineral density and increased fracture risk in healthy elderly women. Animal studies have shown that the most potent form of vitamin K is vitamin K2, which was administered to rats at 0.1 mg/kg orally (Akiyama, Y., K. Hara, A. Matsumoto, S. Takahashi, and T. Tajima, 1995, Comparison of intestinal absorption of vitamin K2 (menaquinone) homologues and their effects on blood coagulation in rats with hypoprothrombinaemia, *Biochem Pharmacol* 49:1801-7). Vitamin K2, in the form of menaquinone-4, is the most biologically active form. It has been extensively studied in the treatment of osteoporosis. In one of these studies, 241 osteoporotic women were given 45 mg/day vitamin K2 and 150 mg elemental calcium. After two years, vitamin K2 was shown to maintain lumbar bone mineral density, significant lower fracture incidence (10% versus 30% in the control group (Shiraki, M., Y. Shiraki, C. Aoki, and M. Miura, 2000, Vitamin K2 (menatetrenone) effectively prevents fractures and sustains lumbar bone mineral density in osteoporosis, *J Bone Miner Res* 15:515-21).

Vitamin K2, but not vitamin K1, may inhibit the calcification of arterial plaque. In 1996, animal studies involving rats found high dose of vitamin K2 (100 mg/kg body weight daily) inhibited the increase in calcium in both kidneys and aorta induced by megadose of synthetic vitamin D (Seyama, Y., M. Horiuch, M. Hayashi, and Y. Kanke, 1996, Effect of vitamin K2 on experimental calcinosis induced by vitamin D2 in rat soft tissue, *Int J Vitam Nutr Res* 66:36-8). A similar study was conducted with rabbits. High dose of Vitamin K2 (1-10 mg/kg daily for 10 weeks) inhibited the atherosclerotic plaque progression in the aorta and pulmonary arteries (Kawashima, H., Y. Nakajima, Y. Matubara, J. Nakanowatari, T. Fukuta, S. Mizuno, S. Takahashi, T. Tajima, and T. Nakamura, 1997, Effects of vitamin K2 (menatetrenone) on athero-sclerosis and blood coagulation in hypercholesterolemic rabbits, *Jpn J Pharmacol* 75:135-43).

Vitamin K2 was also seen to reduce total cholesterol levels, lipid peroxidation, ester cholesterol deposition in the aorta and factor X activity in plasma compared to the control group. A study involving more than 500 postmenopausal women investigated the relation between vitamin K1 and vitamin K2 intake and coronary calcification. Sixty-two percent of the women sampled for the study had coronary calcification. Only vitamin K2 intake was associated with the trend toward decreasing coronary calcification (Beulens, J. W., M. L. Bots, F. Atsma, M. L. Bartelink, M. Prokop, J. M. Geleijnse, J. C. Witteman, D. E. Grobbee, and Y. T. van der Schouw, 2009, High dietary menaquinone intake is associated with reduced coronary calcification, Atherosclerosis 203:489-93).

In some embodiments, a composition of the present disclosure comprises one or more of the vitamins or vitamers above. A composition may comprise one or more of the vitamins or vitamers above in amounts between 1 µg and 1,000 mg per dose.

In some embodiments, a composition of the present disclosure may further comprise antioxidant compounds. These may include, but are not limited to, nonenzymatic compounds such as tocopherol (aTCP), coenzyme Q10 (Q), cytochrome c (C) and glutathione (GSH), and enzymatic components such as manganese superoxide dismutase (Mn-SOD), catalase (Cat), glutathione peroxidase (GPX), phospholipid hydroperoxide glutathione peroxidase (PGPX), glutathione reductase (GR); peroxiredoxins (PRX3/5), glutaredoxin (GRX2), thioredoxin (TRX2) and thioredoxin reductase (TRXR2). A composition may comprise one or more of the antioxidant compounds above in amounts between 1 µg and 1000 mg per dose.

In some embodiments, a composition of the present disclosure may further comprise a stabilized oxidative species. The stabilized oxidative species may be, without limitation, one or more of $H_2O$, $O_2$, $H_2O_2$, $Cl_2O$ and $H_3O$.

Other adjuncts may include selenium and/or selenocysteine at concentrations of 60 to 90 µg per dose. Other adjuncts may also include other trace elements and their salts, including, but not limited to, copper, chromium, iodine, fluoride, zinc, manganese, molybdenum, and iron.

In some embodiments, compositions of the present disclosure may be formulated by combining pharmaceutical grade compounds into a stable therapeutic composition. Compounds may be added in desired amounts to a vessel, with water added to complete a final volume. In some embodiments, a composition of the present disclosure comprises a final volume of between 5 mL and 500 mL. In other embodiments, a composition comprises a final volume of about 250 mL. In some embodiments, the composition may be provided in 20 mL vials. A composition of the present invention may be further diluted prior to administration. For example, a 20 mL vial may be diluted with saline to a 100 mL dispensed volume for administration. In other embodiments, the liquid formulation may be reduced to dry solid via lyophilization. The lyophilized formulation may then be reconstituted to a particular volume prior to administration.

Table 1 shows various formulations of the composition according to exemplary embodiments of the present disclosure per 20 mL vial:

TABLE 1

| Component | mg/dose | mg/dose | mg/dose | mg/dose | mg/dose | mg/dose | mg/dose | mg/dose |
|---|---|---|---|---|---|---|---|---|
| L-Ascorbic Acid USP | 0 | 450 | 900 | 900 | 12 | 2,000 | 2,000 | 0 |
| Dehydroascorbic Acid | 0 | 0 | 0 | 12 | 900 | 2,000 | 2,000 | 4,000 |
| Thiamine HCl USP | 63.33 | 63.33 | 63.33 | 63.33 | 63.33 | 63.33 | 63.33 | 63.33 |
| Magnesium Sulfate USP | 808 | 808 | 808 | 808 | 808 | 808 | 808 | 808 |
| Cyanocobalamin USP | 1.93 | 1.93 | 1.93 | 1.93 | 1.93 | 1.93 | 1.93 | 1.93 |
| Niacinamide USP | 119 | 119 | 119 | 119 | 119 | 119 | 119 | 119 |
| Pyridoxine HCl USP | 119 | 119 | 119 | 119 | 119 | 119 | 119 | 119 |
| Riboflavin 5'Phosphate USP | 2.53 | 2.53 | 2.53 | 2.53 | 2.53 | 2.53 | 2.53 | 2.53 |
| Calcium D-Pantothenate USP | 2.93 | 2.93 | 2.93 | 2.93 | 2.93 | 2.93 | 2.93 | 2.93 |
| Sodium Bicarbonate USP | 840 | 840 | 840 | 840 | 840 | 3,360 | 3,360 | 3,360 |
| WFI (water for injection) | balance | balance | balance | balance | balance | balance | balance | balance |
| HCl USP diluted with WFI (mM @ 20 ml) | 250 | 125 | 0 | 6.5 | 6.5 | 0 | 250 | 0 |

In some embodiments, the components of the compositions in Table 1 may be varied from the listed values by plus or minus 1%, 2%, 5%, or 10% according to therapeutic need. The compositions of Table 1 may also further comprise additional components as described above according to therapeutic need.

In some embodiments, compositions of the present disclosure may be stabilized to enhance shelf life. The compositions may be stabilized by suitable techniques as known to those of ordinary skill in the art, including, but not limited to, freezing, lyophilization, use of UV or spectral blocking vials (e.g., amber vials), overfilling with stabilizing gases such as nitrogen, bubbling a stabilizing gas through the solution, separating reactive species into multiple vials to be combined upon use, and cold chain storage. As one non-limiting example, the acid and buffer components of a composition may be separated into two vials. Other components of compositions of the present disclosure (e.g., cyanocobalamin, calcium d-pantothenate, and/or others) may be included in these vials or further separated into additional vials.

Methods of Treatment

In another aspect, the present disclosure provides methods of treatment. The methods of the invention involve administering the composition of the invention to subjects in need thereof.

One embodiment of the invention is a method of treating or ameliorating a mitochondrial disorder, metabolic disorder, a condition associated with diabetes, a cardiovascular dysfunction, or an ocular condition in a subject in need thereof, by administering to the subject a stable therapeutic composition of the present disclosure.

Mitochondrial dysfunction, characterized by a loss of efficiency in the electron transport chain and reductions in the synthesis of high-energy molecules, such as ATP, is a characteristic of aging, and essentially, of all chronic diseases. As used herein, the term "mitochondrial disorder" refers to a condition or disorder characterized by mitochondrial dysfunction, and includes, for example, neurodegenerative diseases, such as Alzheimer's disease, Parkinson's disease, Huntington's disease, amyotrophic lateral sclerosis, and Friedreich's ataxia, cardiovascular diseases, such as atherosclerosis and other heart and vascular conditions, diabetes and metabolic syndrome, autoimmune diseases, such as multiple sclerosis, systemic lupus erythematosus, and type 1 diabetes, neurobehavioral and psychiatric diseases, such as autism spectrum disorders, schizophrenia, and bipolar and mood disorders, gastrointestinal disorders, fatiguing illnesses, such as chronic fatigue syndrome and Gulf War illnesses, musculoskeletal diseases, such as fibromyalgia and skeletal muscle hypertrophy/atrophy, and chronic infections.

As used herein, a "metabolic disorder" refers to diabetes, insulin resistance, glucose intolerance, hyperglycemia, hyperinsulinemia, obesity, hyperlipidemia, or hyperlipoproteinemia. The terms "diabetes" and "diabetes mellitus" are intended to encompass both insulin dependent and non-insulin dependent (Type 1 and Type 2, respectively) diabetes mellitus, gestational diabetes, as well as pre-diabetes, unless one condition or the other is specifically indicated.

As used herein, a "condition associated with diabetes" includes obesity, hypertension, hyperlipidemia, fatty liver disease, nephropathy, neuropathy, renal failure, retinopathy, diabetic ulcer, cataracts, insulin resistance syndromes and cachexia.

As used herein, "cardiovascular dysfunction" includes conditions and diseases such as coronary heart disease, cerebrovascular disease, hypertension, peripheral artery disease, occlusive arterial disease, angina, rheumatic heart disease, congenital heart disease, heart failure, cardiac insufficiency, palpitations, supraventricular tachycardia, fibrillation, faintness, dizziness, fatigue, migraine, high levels of total blood cholesterol and/or LDL cholesterol, low level of HDL cholesterol, high level of lipoprotein, infections of the heart such as carditis and endocarditis, diabetic ulcer, thrombophlebitis, Raynaud's disease, anorexia nervosa, claudication and gangrene, atherosclerosis and peripheral artery disease. Diseases and conditions that are especially suited for treating or ameliorating with a pharmaceutical grade buffer composition as described herein are peripheral artery disease and atherosclerosis.

As used herein, the term "ocular condition" refers to pathological conditions pertaining to the eye, and may include, but is not limited to, glaucoma, macular degeneration, light sensitivity issues, calcific and collagen-based floaters, lens rigidity correction.

Another embodiment of the invention is a method of treating or ameliorating a dermatological condition by administering to the subject a stable therapeutic composition of the present disclosure; As used herein, the term "dermatological condition" refers to skin-related disorders, conditions and disease such as skin aging, wrinkles (including, e.g., laugh lines and wrinkles surrounding the eye), acne, photodamage, rosacea, scars, eczema, alopecia, hypertrophic scars, keloids, stretch marks or Striae distensae, psoriasis, pruritus, ehlers-danlos syndrome, scleroderma, post inflammatory hyperpigmentation, melasma, alopecia, poikiloderma of civatte, vitiligo, skin dyschromia, burns and blotchy pigmentation.

In another aspect, the present disclosure provides a method of modifying the metabolism of a subject, the method comprising administering to the subject a stable therapeutic composition comprising a buffer solution comprising at least one pharmaceutical grade acid and at least one pharmaceutical grade pH buffering agent, wherein the buffer solution is sufficient to reduce the physiological bloodstream pH of a subject by 0.01 to 1.1, and wherein the buffer solution has a buffer capacity sufficient to sustain the reduction of the physiological bloodstream pH of the subject for between 1 minute and 1 week.

A different embodiment of the invention provides a method of reducing lactate burden in a subject in need thereof, by administering to the subject the composition of the invention. The reduction of lactate burden has been described extensively herein-above.

In another embodiment of the invention, the present disclosure provides a method of reducing acidosis in a subject in need thereof, by administering to the subject the composition of the invention. The reduction of acidosis has been described extensively herein-above.

In another embodiment, the present disclosure provides a method of treating a central nervous system disorder in a subject in need thereof, by administering the composition of the invention. As used herein, the term "central nervous system disorder" means any neurological disorder affecting the structure or function of the brain or spinal cord.

In another embodiment, the present disclosure provides a method of treating chronic wounds of a subject, by administering the composition of the invention. In some embodiments, the present disclosure provides a method for inducing accelerated wound healing in a subject, the method by administering a stable therapeutic composition of the present disclosure.

In another embodiment, the present disclosure provides a method of enhancing mental or physical performance of a subject, by administering the composition of the invention.

Routes of administration for a therapeutically effective amount of a composition of the present disclosure include, but are not limited to, intravenous, intramuscular, or parenteral administration, oral administration, otic administration, topical administration, inhalation or otherwise nebulized administration, transmucosal administration and transdermal administration. Compositions of the present disclosure may also be formulated for intravenous, bolus, dermal, oral, otic, suppository, buccal, ocular, or inhalation delivery. For intravenous or parenteral administration, i.e., injection or infusion, the composition may also contain suitable pharmaceutical diluents and carriers, such as water, saline, dextrose solutions, fructose solutions, ethanol, or oils of animal, vegetative, or synthetic origin. It may also contain preservatives, and buffers as are known in the art. When a therapeutically effective amount is administered by intravenous, cutaneous or subcutaneous injection, the solution can also contain components to adjust pH, tonicity, stability, and the like, all of which is within the skill in the art. For topical administration, the composition may be formulated in, e.g., liquid, gel, paste, or cream. In some embodiments, the composition may be administered via a topical patch. For ocular administration, the composition may be formulated in, e.g., liquid eye drops, or as a gel, paste, or cream to be applied to the surface of the eye and/or surrounding tissue. For otic administration, the composition may be formulated in, e.g., ear drops.

A composition for intravenous, cutaneous, or subcutaneous injection should contain, in addition to peptide an isotonic vehicle such as Sodium Chloride Injection, Ringer's Injection, Dextrose Injection, Dextrose and Sodium Chloride Injection, Lactated Ringer's Injection Citrate Buffer pH 5.5, or other carriers, diluents and additives as known in the art. As described fully elsewhere herein, the pharmaceutical composition of the present invention may also contain stabilizers, preservatives, buffers, antioxidants, or other additive known to those of skill in the art. The pharmaceutical compositions are formulated for intravenous or parenteral administration. Typically, compositions for intravenous or parenteral administration comprise a suitable sterile solvent, which may be an isotonic aqueous buffer or pharmaceutically acceptable organic solvent.

As described fully elsewhere herein, where necessary, the compositions can also include a solubilizing agent. Compositions for intravenous or parenteral administration can optionally include a local anesthetic to lessen pain at the site of the injection. Generally, the ingredients are supplied either separately or mixed together in unit dosage form in a hermetically sealed container such as an ampoule or sachet. The pharmaceutical compositions for administration by injection or infusion can be dispensed, for example, with an infusion bottle containing, for example, sterile pharmaceutical grade water or saline. Where the pharmaceutical compositions are administered by injection, an ampoule of sterile water for injection, saline, or other solvent such as a pharmaceutically acceptable organic solvent can be provided so that the ingredients can be mixed prior to administration.

The duration of intravenous therapy using the pharmaceutical composition of the present invention will vary, depending on the condition being treated or ameliorated and the condition and potential idiosyncratic response of each individual mammal. The duration of each infusion is from <1 minute (e.g., bolus injection) to about 1 hour (intravenous delivery). The infusion can be repeated within 24 hours. Thus, a mammal can receive about 1 to about 25 infusions per day. Preferably, the number of infusions per day is 1 or 2. The period between each infusion can be 1, 2, 5, 10, 20, 30, 40, 50 minutes, or 1, 2, 3, 4, 5, 6, 7, 8, 9, 10, 11, 12 hours or more. The administration may also be administered at any of a variety of cadences, including hourly, daily, weekly, monthly, quarterly, bi-annually, annually, etc., or any other particular timeframe depending on the condition to be treated and/or the response of each individual mammal. In other embodiments, a pharmaceutical composition of the present invention may be administered as a single event, or may be administered over week-long, multi-week, month-long, year-long, or multi-year durations, or for any other desired duration as may be warranted.

Alternatively, the infusions can be given one after another without a substantial period in between. In one embodiment, the infusion lasts about 45 minutes. The dose may be repeated 2-3 times a week depending on the severity of the relative or absolute deficits of nutrients in the patient. A clinical assessment may be necessary in order to establish the status, but can be limited to a review of medical history, subjective review of symptoms, the subjective opinion of the mammal when human or upon review of any specific deficits.

In another embodiment of administration, administration is alternated between two solutions: one acid shifting (AS) and one base shifting (BS) as described above. Alternating administration of AS/BS/AS/BS in various cadences would be expected to induce more pH swings from acidic towards basic or from basic towards acidic. Such events, as induced through exercise, are recognized for their value in promoting nitric oxide (NO) release for vasodilation (Capellini, Verena K., et al., 2013, The Effect of Extracellular pH Changes on Intracellular pH and Nitric Oxide Concentration in Endothelial and Smooth Muscle Cells from Rat Aorta, PLOS One, 8(5):e62887), and to promote cardiolipin repair and remodeling (Khalafat, Nada, et al., 2011, Lipid Packing Variations Induced by pH in Cardiolipin-Containing bilayers: The Driving Force for the Cristae-Like Shape Instability, Biochimica et Biophysica Acta—Biomembranes, 1808(11): 2724-2733). These alternating administrations may each last between 0.5 and 60 minutes, and may be alternated one, two, or more times as necessary to achieve the desired therapeutic effect. The AS and BS administrations need not necessarily be identical in either their shifting effect or duration of administration. That is, for example, an AS composition may affect a larger shift over a shorter administration, while the BS composition may affect a smaller shift over a longer administration. In some embodiments, an exemplary administration profile may be a 5 minute AS administration followed by a 10 minute BS administration, repeated two times (i.e., 5/10/5/10). Other exemplary administration profiles may be, e.g., 10/10/10/10 or 0.5/0.5/0.5/0.5.

Systemic formulations include those designed for administration by injection, e.g., subcutaneous, intravenous, intramuscular, intrathecal or intraperitoneal injection. Useful injectable preparations include sterile suspensions, solutions or emulsions of the active compound(s) in aqueous or oily vehicles. The compositions also can contain solubilizing agents, formulating agents, such as suspending, stabilizing and/or dispersing agent. The formulations for injection can be presented in unit dosage form, e.g., in ampules or in multidose containers, and can contain added preservatives. For prophylactic administration, the compound can be administered to a patient at risk of developing one of the previously described conditions or diseases. Alternatively, prophylactic administration can be applied to avoid the onset of symptoms in a patient suffering from or formally diagnosed with the underlying condition.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art coupled with the general and specific examples disclosed herein.

Formulations can comprise other ingredients for the treatment of the organism as a whole. For example, an antioxidant additive and/or pro-oxidant additive can be present. The latter may be an agent that acts as a preventive, while the former may be an agent that acts to treat a specific medical condition.

Efficacy of treatment may be determined by measuring biomarkers before, during, and/or after administration of a composition of the present disclosure, or before, during and/or after administration of a course of treatment using compositions of the present disclosure. Exemplary biomarkers, and the indications for which they may be used, are shown in Table 2, and may include, e.g., AlMicro, tubular disorders and electrolyte imbalance; A2Macro, cerebral small vessel disease, liver fibrosis; ACE, high blood pressure, heart failure, diabetic nephropathy; Adiponectin, vascular disease, metabolic syndromes; Apo A-I, high density lipid particles; Apo A-II, HDL metabolism; Apo C-II, ischemic stroke, heart disease; Apo C-III, metabolic syndrome and hypertriglyceridemia; Apo H, type 2 diabetes, metabolic syndrome; AT-III, venous thrombosis, abnormal coagulation; B2M, peripheral arterial disease; BDNF, psychiatric disorders; CD163, HIV infection, inflammation, cardiovascular disease; CD40, atherosclerotic instability; CD40-L, cellular proliferation; CgA, tumors; C-Peptide, metabolic syndrome; CRP, inflammation and tissue damage; Cystatin-C, cardiovascular disease, electrolyte imbalance; EGF, cellular proliferation; EN-RAGE, inflammation, heart disease; EPO, anemia, chronic kidney disease; E-Selectin, inflammation, electrolytic imbalances; Factor VII, thrombosis (blood clotting); Ficolin-3, diabetic peripheral neuropathy; FRTN, blood disorders, anemia; FSH, pregnancy complications; GDF-15, mitochondrial diseases; GLP-1 total, type 2 diabetes, insulin secretion; HB-EGF, epithelial cell proliferation (inflammation); ICAM-1, inflammation; IFN-gamma, inflammation and immune response; IL-1 alpha, inflammation; IL-1 beta, inflammation; IL-10, inflammation; IL-12p40, inflammation, multiple sclerosis, Alzheimer's disease; IL-12p70, peritonitis, inflammation; IL-15, Alzheimer's disease; IL-17, inflammation, lupus, cerebral vasculitis; IL-18, metabolic syndrome, acute kidney injury; IL-1ra, inflammation; IL-2, inflammation; IL-23, inflammation, lupus; IL-3, inflammation, cell growth, proliferation, and differentiation; IL-4, inflammation; IL-5, inflammatory factors, asthma, chronic obstructive pulmonary disease; IL-6, inflammation; IL-6r, coronary heart disease; IL-7, immune-mediated inflammatory diseases; IL-8, inflammation; IP-10, tuberculosis related complications; LH, infertility; Lp(a), cardiovascular diseases; MCP-1, inflammation; MCP-2, tuberculosis; MCP-4, asthma, metastasis; M-CSF, metabolic, hematologic and immunologic abnormalities; MIG, heart failure and left ventricular dysfunction; MIP-1 alpha, cytokine expression for high fat diet, wound healing; MIP-1 beta, autoimmune disorders; MIP-3 alpha, tissue injury in ischemic stroke and autoimmune diseases; MMP-3, ischemic and hemorrhagic stroke; MMP-9, ischemic and hemorrhagic stroke; MPIF-1, Kawasaki disease (inflammation in the walls of some blood vessels); MPO, inflammation and ischemia; Myoglobin, inflammation and ischemia; NAP-2, hepatitis B; NGF-betac, Alzheimer's disease, psychological disorders; Nr-CAM, Alzheimer's disease, cognitive disorders; Osteocalcin, osteoporosis, bone formation; PAI-1, metabolic syndrome; PARC, Gaucher disease (enlargement of liver/spleen); PDGF-BB, osteoblast development and bone formation, liver fibrosis; PEDF, cardiometabolic disorders; Periostin, asthma; PLGF, angiogenesis, vasculogenesis and lymphangiogenesis; PPP, endocrine pancreatic tumors; PRL; P-Selectin, inflammation; RAGE, chronic inflammatory diseases; RANTES, abdominal aortic aneurysm, viral diseases; Resistin, inflammation, cardiovascular disease; S100-B, brain damage and blood-brain barrier disruption; SAA, inflammation; SAP, acute and chronic inflammation; SCF, tumor proliferation; SHBG, thyroid disorders, pituitary diseases; SOD-1, amyotrophic lateral sclerosis; Sortilin, coronary artery disease, affective disorders; ST2, inflammation and adhesion; TAFI, arterial thrombosis, acute ischemia; TBG, thyroid related disorders; TIMP-1, tissue remodeling, wound healing and tumor metastasis; TN-C, myocarditis; TNF-alpha, inflammation; TNF-beta, inflammation, cardiovascular disease; TNFR2, ischemic stroke, insulin disorders; TTR, metabolic and septic disorders; VCAM-1, inflammation; VEGF, angiogenesis, hypoxia; Vitronectin, Alzheimer's disease; and vWF, arrhythmia, acute arterial damage.

TABLE 2

| Tier II Biomarkers | Reference Range | Regulation during diseased state | Pathological relevance |
|---|---|---|---|
| E-Selectin | 30 pg/ml-18000 pg/ml* | Up | Inflammation |
| L-Selectin | 100 pg/ml-25 ng/ml | Up | Inflammation |
| P-Selectin | 20 pg/ml-30 ng/ml | Up | Inflammation |
| Intercellular Adhesion Molecule-1 (ICAM-1) | 150 pg/ml-20 ng/ml | Up | Inflammation |
| Vascular Cell Adhesion Molecule-1 (VCAM-1) | 0.3 ng/ml-60 ng/ml | Up | Inflammation |
| Epidermal Growth Factor (EGF) | 1 pg/ml-200 pg/ml | Up | Cellular Proliferation |
| Interferon-g (IFN-g) | 15.6-1,000 pg/mL | Up | Inflammation and Immune Response |
| Interleukin-1a (IL-1a) | 0.5 pg/ml-300 pg/ml | Up | Inflammation |
| Interleukin-1b (IL-1b) | 0.3 pg/ml-100 pg/ml | Up | Inflammation |
| Interleukin-2 (IL-2) | 4 pg/ml-1,500 pg/ml | Up | Inflammation |
| Interleukin-4 (IL-4) | 5 pg/ml-200 pg/ml | Up | Inflammation |
| Interleukin-6 (IL-6) | 3 pg/ml-1,000 pg/ml | Up | Inflammation |
| Interleukin-8 (IL-8) | 1 pg/ml-600 pg/ml | Up | Inflammation |
| Interleukin-10 (IL-10) | 1 pg/ml-150 pg/ml | Up | Inflammation |
| Monocyte Chemotactic Protein-1 (MCP-1) | 2 pg/ml-500 pg/ml | Up | Inflammation |
| Tumour Necrosis Factor-a (TNF-a) | 30 pg/ml-6,000 pg/ml | Up | Inflammation |
| Vascular Endothelial Growth Factor (VEGF) | 31-86 pg/mL | Up | Hypoxia |
| SAA | 0.5 ng/ml-300 ng/ml | Up | Inflammation |
| Fibrinogen | 150-400 mg/dL | Up | Thrombosis |
| C-Reactive Protein (CRP) | 0-10 mg/dL | Up | Inflammation and Tissue Damage |
| Apo A1 | Males: 94-176 mg/dL; Females: 101-198 mg/dL | Up | Hight Density Lipid Particles |
| Apo B | Male: 52-109 mg/dL; Female: 49-103 mg/dL | Up | Low Density Lipid Particles |
| Insulin | 4 µIU/ml-300 pIU/ml | Up | Metabolic Syndrome |
| Proinsulin | 0.313 ng/ml-20 ng/ml | Up | Metabolic Syndrome |
| C-peptide | 0.156 ng/ml-10 ng/ml | Up | Metabolic Syndrome |
| Myeloperoxidase | Adult Male = ≤50 mcg/L; Adult Female = ≤30 mcg/L | Up | Inflammation and Ischemia |
| CD40 Ligand | 32-2,000 pg/mL | Up | Cellular Proliferation |
| Bile Acid Panel (16 bile acids) | Varies | Varies | Cardiovascular Disease |
| p180 Kit (188 endogenous metabolites from 5 compound classes) | Varies | Varies | Cardiometabolic Risk |
| Oxidized LDL | 30-2,000 pg/mL | Up | Oxidative Stress and Low Density Lipid Particle |
| ST2 | 0.156--10 ng/mL | Up | Inflammation and Adhesion |
| Creatine Kinase Muscle Brain (CK-MB) | 0-5.0 ng/mL | Up | Inflammation |
| Heart Type Fatty Acid Binding Protein (H-FABP) | 102-25,000 pg/ml | Up | Inflammation and Thrombosis |
| Myoglobin (Myo) | Adult Male = ≤50 mcg/L; Adult Female = ≤30 mcg/L | Up | Inflammation and Ischemia |

TABLE 2-continued

| Tier II Biomarkers | Reference Range | Regulation during diseased state | Pathological relevance |
|---|---|---|---|
| Troponin I (cTnI) | ≤0.05 ng/mL | Up | Cardiovascular Disease |
| Adiponectin | 0.38-12 ng/mL (www.k-assay.com) | Up | Inflammation and Cardiac Disease |
| Cystatin C | 0.3 ng/ml-20 ng/ml | Up | Cardiovascular Disease |
| Catalase | 0.313 ng/ml-20 ng/ml | Up | Oxidative Stress |
| p53 | 3.1 U/ml-100 U/ml | Down | Apoptosis |

Kits

One embodiment of the invention includes a kit for administering the stable therapeutic composition of the present disclosure to a subject. In this embodiment, the kit may contain the composition in a single vial or in more than one vial. The vial can preferably be an injection vial with a membrane that is suitable for inserting a syringe to pull the solution from the vial or a soft I.V. infusion bag. The composition of the invention is contained in the vial in a sterile aqueous solution. The solution can be provided as a concentrated solution to which a diluent is added prior to administration. The diluent can be sterile water. The kit may further comprise a pre-filled container which contains the diluent. In a preferred embodiment, a soft infusion bag is pre-filled with diluent. Alternatively, the composition vial can contain a solution that is at a concentration which is suitable for injection without any dilution. Preferably, the solution for injection is isotonic. That is, the solution can contain salt, carbohydrates, such as glucose, $NaHCO_3$ or amino acids, such as glycine, and is isotonic with blood plasma. In other instances, the solution may be hypotonic so as to promote more rapid intracellular uptake or hypertonic so as to promote slower intracellular uptake.

In one embodiment of the invention, the kit contains two vials. The first vial at least one pharmaceutical grade acid in a sterile aqueous solution. For example, the first vial may contain pharmaceutical grade ascorbic acid, thiamine HCl, magnesium sulfate, cyanocobalamin, niacinamide, pyroxidine HCl, riboflavin 5' phosphate, calcium D-pantothenate, and an aqueous solvent containing sodium chloride and water (for injection). The second vial contains at least one pharmaceutical grade pH buffering agent in a sterile aqueous solution. For example, the second vial may contain pharmaceutical grade sodium bicarbonate and an aqueous solvent containing sodium chloride and water (for injection). The contents of the vials may be stored under refrigeration or under freezing conditions.

In another embodiment, the kit may contain a container of a lyophilized powder that may be reconstituted prior to administration. The lyophilized powder may be an isotonic solution.

Each kit described herein may further comprise instructions for use. The instructions will, of course, depend upon the kit itself and whether a diluent is to be used or other components to be admixed with the pharmaceutical grade buffer solution prior to administration.

EXAMPLES

Example 1

Experiments described herein were designed to validate key aspects of using buffered acidic solutions to acidically shift bloodstream pH for therapeutic purposes. Specifically, several aspects are illustrated: (1) Blood has acid-base properties that can be notionalized as a solution having a physiological pH and buffer capacity. Furthermore, therapeutic compositions designed to shift blood pH upon administration can be notionalized as solutions having a target pH and buffer capacity. (2) pH shifting of the bloodstream towards acidic conditions can be achieved via intravenous or intraarterial administration of an acid solution. (3) Alternative formulations having higher concentrations of buffer components have increased capacity to impede the restoration of bloodstream pH back towards physiologic. (4) Faster dissolution of calcified mineral forms can be achieved when the conditions are shifted from equilibrium at a given pH to lower pH levels.

The rationale, protocol, and results of these experiments are described in the following sections.

Acid-Base Properties of Blood

At physiologic norm conditions, blood is recognized to commonly have a pH value near 7.41. The is due to the presence of various acids within it (primarily HCl) and various buffers (primarily bicarbonate). In the interest of developing a surrogate to emulate the acid-base properties of blood, a water-based solution was prepared that contained HCl and HCO3. HCl and HCO3 were chosen for this surrogate as they are the primary acid and buffer species in blood. For this blood surrogate, 0.0024 M HCl in 5,000 ml of aqueous solution was buffered with 0.025 M of $NaHCO_3$, to produce a resultant pH of 7.41 (Table 3). This surrogate was freshly prepared for each of the tests that were performed as $CO_2$ loss will influence the pH over time if left to atmospheric exposure.

Similarly, drug products designed to shift blood pH could be formulated using a variety of physiologically compatible acids and buffers. To illustrate this, 4 example drug products (C1-C4: Table 3) were formulated using HCl and NaHCO3 as example acid and buffer components (Blood and Drug Compositions per Table 3 Below). By design, these would have pH below physiologic and be comprised of buffer products as well. C1 was designed to provide a small pH shift for a short time, C2 was designed to provide a small pH shift for a long time, C3 was designed to provide a large pH shift for a short time, and C4 was designed to provide a large pH shift for a long time.

TABLE 3

| | Volume (ml) | HCO3-(Bicarbonate) pKa 6.4 | | | pH = pKa + log10 (base/acid) | | | |
|---|---|---|---|---|---|---|---|---|
| | | HCO3- concentration (M/L) | HCO3- amount (mM) | pH = pI calc pH | actual pH | HCl concentration (M/L) | HCl amount (mM) | |
| C1: large shift long time | | | | | | | | |
| C1: large shift long time | 20 | 0.5000 | 10 | 6.75 | 6.98 | 0.2233 | 4.5 | pH shift of |
| Blood | 5000 | 0.0250 | 125 | 7.41 | 7.41 | 0.0024 | 12.2 | blood + C1 |
| Blood + Cl | 5020 | 0.0269 | 135 | 7.31 | 7.31 | 0.00332 | 16.7 | per added |
| Bicarb restoring force | | | 10 | | | | | gram of BiCarb |
| Blood + Cl + BiCarb | 5020 | 0.0289 | 145 | 7.34 | 7.41 | 0.00332 | 17 | 0.010 |
| C2: large shift long time | | | | | | | | |
| C2: large shift long time | 20 | 2.0000 | 40 | 7.10 | 7.24 | 0.3991 | 8.0 | pH shift of |
| Blood | 5000 | 0.0250 | 125 | 7.41 | 7.41 | 0.0024 | 12.2 | blood + C2 |
| Blood + C2 | 5020 | 0.0329 | 165 | 7.31 | 7.31 | 0.00402 | 20.2 | per added |
| Bicarb restoring force | | | 10 | | | | | gram of BiCarb |
| Blood + C2 + BiCarb | 5020 | 0.0349 | 175 | 7.34 | 7.35 | 0.00402 | 20 | 0.004 |
| C3: large shift long time | | | | | | | | |
| C3: large shift long time | 20 | 0.5000 | 10 | 5.66 | 5.75 | 2.7477 | 55.0 | pH shift of |
| Blood | 5000 | 0.0250 | 125 | 7.41 | 7.41 | 0.0024 | 12.2 | blood + C3 |
| Blood + C3 | 5020 | 0.0269 | 135 | 6.70 | 6.70 | 0.01338 | 67.2 | per added |
| Bicarb restoring force | | | 30 | | | | | gram of BiCarb |
| Blood + C3 + BiCarb | 5020 | 0.0329 | 165 | 6.79 | 6.95 | 0.01338 | 67 | 0.008 |
| C4: large shift long time | | | | | | | | |
| C4: large shift long time | 20 | 2.0000 | 40 | 6.15 | 6.11 | 3.5566 | 71.1 | pH shift of |
| Blood | 5000 | 0.0250 | 125 | 7.41 | 7.41 | 0.0024 | 12.2 | blood + C4 |
| Blood + C4 | 5020 | 0.0329 | 165 | 6.68 | 6.70 | 0.01660 | 83.3 | per added |
| Bicarb restoring force | | | 50 | | | | | gram of BiCarb |
| Blood + C4 + BiCarb | 5020 | 0.0428 | 215 | 6.81 | 6.92 | 0.01660 | 83 | 0.004 |

First, C1, C2, C3, and C4 were formulated, as was the blood surrogate, and the pH was measured. The pH was also calculated per the Henderson-Hasselbalch equation. Second, the compositions C1, C2, C3, and C4 were added to the surrogate blood. Again, a pH value was calculated, and a pH value was measured. Upon administration into the bloodstream, each of the example therapeutic solutions shift the bloodstream pH from physiologic norm conditions (e.g., 7.41 pH) to reduced pH (e.g., 7.31-6.70 pH). This is demonstrated through addition of the C1 (or 2, 3, 4) to the blood surrogate solution, as summarized in Table 3. In this case, the therapeutic formulations with the lowest pH and/or larger buffer fraction are capable of imparting a larger shift in bloodstream pH.

To demonstrate the resilience of therapeutically shifted blood to resist return to physiologic, a fixed quantity of bicarbonate was added into each of the therapeutically shifted blood solutions. This was done to simulate pH restoring effects such as stimulation of additional buffer sources, $CO_2$ respiration, and renal action to remove $H^+$ and re-cycling of $HCO_3^-$. Such restorative forces were simulated by administering a fixed allocation of $HCO_3^-$ to the therapeutically shifted blood surrogate solution. For a given quantity of added bicarbonate, the differing resilience of the C1-C4 compositions to resist blood pH restoration could be demonstrated. As shown in Table 3, the resilience to restoration can be expressed in terms of delta pH/gram $HCO_3$, where a lower value implies a greater capacity to resist pH restoration forces. In this example, the formulations with more buffer capacity (C2 or C4) are more resistant to restore towards physiologic per gram of pH restoring bicarbonate added.

To demonstrate the ability of calcium salts to dissolve more readily in lower pH solutions, such as would be the case for calcified plaques in a pH-shifted bloodstream, calcium salts were submerged in therapeutically pH-shifted blood surrogate solution and dry weighed after select time intervals of submersion.

To this end the blood surrogate was first exposed to a large quantity of calcium salt for an extended period while at pH 7.41 to establish equilibrium of the salt at the start pH. Then residual solid calcium salts were removed, leaving a blood surrogate solution that was near-saturated with the calcium salt at the 7.41 pH. Then C1 (or 2, 3, 4) formulations were added to the calcium saturated blood surrogate to reduce the pH. Then the 2 g pellets of the calcium salts were submerged in therapeutically pH-shifted solution and dry weighed at select time intervals to establish a rate of weight loss (Table 4). Because the surface area and shape of the calcium mineral was common to all tests, the test demonstrates that lower pH solutions promote higher dissolution rates than higher pH solutions (~0.043-0.044 g/min for pH 7.31 vs 0.054-0.059 g/min for pH=6.7)).

TABLE 4

| Time minutes | Ca2+ weight (g) | Rate of Dissolution (g/min) |
|---|---|---|
| C1 Bloodstream pH 7.31 | | |
| 10 | 1.9667 | |
| 20 | 1.5257 | 0.044 |

TABLE 4-continued

| Time minutes | Ca2+ weight (g) | Rate of Dissolution (g/min) |
|---|---|---|
| C2 Bloodstream pH 7.31 | | |
| 10 | 1.9578 | |
| 20 | 1.5267 | 0.043 |
| C3 Bloodstream pH 6.7 | | |
| 10 | 1.9887 | |
| 20 | 1.4517 | 0.054 |
| C4 Bloodstream pH 6.7 | | |
| 10 | 1.978 | |
| 20 | 1.3901 | 0.059 |

It will be apparent to one of ordinary skill in the art that various combinations and/or modifications and variations can be made in the compositions of the present disclosure depending upon and as dictated by the therapeutic needs of the patient. Moreover, features illustrated or described as being part of one embodiment may be used on another embodiment to yield a still further embodiment.

Example 2

Studies were conducted by administering the therapeutic composition to three horses. The following materials were prepared for the study:

1. Subject 1—mare, 34 years old, Welsh Cross, 739 pounds, with a history of pre-diabetes, Laminitis with Cushing's disease, and Lymes presentation.
2. Subject 2—male neutered (gelding), 13 years old, Welsh Cross, 724 pounds, history of Laminitis with Cushing's disease, and Lymes presentation.
3. Subject 3—mare, 12 years old, Welsh Cross, 652 pounds, history of Lymes presentation.
4. Each Treatment involved the administration of an intravenous buffer solution:
   a. 100 ml of A-Vial AS* Solution (containing ascorbic acid, hydrochloric acid, and aqueous solvent containing sodium chloride and water), or 100 ml of A-Vial ASVM** Solution (containing ascorbic acid, dehydroascorbic acid, hydrochloric acid, thiamine HCl, magnesium sulfate, cyanocobalamin crystalline, niacinamide, pyroxidine HCl, riboflavin 5' phosphate, and calcium D-pantothenate, and aqueous solvent containing sodium chloride and water).
   b. 100 ml of B-Vial Bicarbonate Solution (containing sodium bicarbonate and an aqueous solvent containing sodium chloride and water).
   c. 1000 ml Saline in an IV-ready bag, or 2000 ml Saline in an IV ready bag.
   * AS—grade sourced Acid Shifting Composition
   ** ASVM—grade sourced Acid Shifting Composition additionally containing select Vitamins and Minerals Methods:

Doses of the therapeutic composition were managed as follows:

TABLE 5

Subject 1 Dosing

| | DOSE 1 DAY 1 | DOSE 2 DAY 2 | DOSE 3 DAY 3 | DOSE 4 DAY 6 | DOSE 5 DAY 8 |
|---|---|---|---|---|---|
| 100 ml A-Vial AS | | | | | |
| 100 ml A-Vial ASVM | X | X | X | X | X |
| 100 ml B-Vial Bicarb | X | X | X | X | X |
| 1000 ml Saline | X | X | X | X | X |
| 2000 ml Saline | | | | | |

TABLE 6

Subject 2 Dosing

| | DOSE 1 DAY 1 | DOSE 2 DAY 2 | DOSE 3 DAY 3 | DOSE 4 DAY 6 | DOSE 5 DAY 8 |
|---|---|---|---|---|---|
| 100 ml A-Vial AS | X | | | | |
| 100 ml A-Vial ASVM | | X | X | X | X |
| 100 ml B-Vial Bicarb | X | X | X | X | X |
| 1000 ml Saline | | X | X | X | X |
| 2000 ml Saline | X | | | | |

TABLE 7

Subject 3 Dosing

| | DOSE 1 DAY 1 | DOSE 2 DAY 2 | DOSE 3 DAY 3 | DOSE 4 DAY 6 | DOSE 5 DAY 8 |
|---|---|---|---|---|---|
| 100 ml A-Vial AS | | | | | X |
| 100 ml A-Vial ASVM | X | X | X | X | |
| 100 ml B-Vial Bicarb | X | X | X | X | X |
| 1000 ml Saline | X | X | X | X | X |
| 2000 nil Saline | | | | | |

Dosing was administered as follows:

A Vial products were refrigerated at 40° F. prior to use, while B Vial products were stored at 70° F. 100 ml of A Vial product was combined into a saline IV bag, and then 100 ml of B Vial product was combined into the IV bag. The IV bag was hung from an elevation point, 18" above infusion point. A catheter was inserted into the jugular vein of the subject. Pre-treatment venous blood samples were extracted from the patient for IDEXX analysis (hematology, chemistry, endocrinology and serology) and blood gas analysis (acid/base status, Oximetry, Electrolytes, metabolites) (T=−5 min). Five minutes (T=0 min) later, the IV bag was connected to a catheter, and the drip was opened to begin infusion. Forty five minutes (T=45 min) later, the drip rate was adjusted to complete infusion. Venous blood samples were extracted from the subject during treatment, 15 minutes (T=15 min) and 30 minutes (T=30 min) after the treatment began. Post-treatment venous blood samples were extracted 60 minutes (T=60 min) and 120 minutes (T=120 min) after the treatment began. Post-treatment sample were subjected to blood gas analysis (acid/base status, Oximetry, Electrolytes and Metabolites)

* Note: Subject 1's "pre-treatment" venous blood samples for IDEXX analysis (hematology, chemistry, endocrinology and serology) were mistakenly sampled 60 minutes after treatment began. The results likely reflect post-dose changes in plasma volume, as large changes were observed for concentration-based markers (e.g., RBC, hematocrit).

Results

Results Section 1: Blood g\Gas and Acid-Base Response:
Subject 2 AS Dose 1 and ASVM Doses 4 and 5: Observed Response: Blood pH, blood $HCO_{3-}$, and oximetry were observed at time intervals of 5 min pre-dose commencement (T=−5), 20 min post dose commencement (T=20), and 5 minutes post-dose complete (dose complete at T=45, measurement at T=50) as shown in Table 8.

TABLE 8

Subject 2 Response for Dose 1 AS, Dose 4 ASVM, Dose 5 ASVM

| | | AS Day 1 Dose 1 | | | ASVM Day 6 Dose 4 | | | ASVM Day 8 Dose 5 | | |
|---|---|---|---|---|---|---|---|---|---|---|
| Time | min | −5 | 20 | 50 | −5 | 20 | 50 | −5 | 20 | 50 |
| pH | — | 7.392 | 7.437 | 7.431 | 7.350 | 7.416 | 7.394 | 7.453 | 7.426 | 7.417 |
| cHCO3− | mmol/L | 33.2 | 31.0 | 31.0 | 26.7 | 26.4 | 26.6 | 29.4 | 27.8 | 27.3 |
| pCO2 | mmHg | 54.5 | 45.9 | 46.5 | 57.3 | 43.2 | 47.7 | 44.3 | 44.5 | 45.1 |
| pO2 | mmHg | 30 | 34 | 35 | 24 | 39 | 31 | 37 | 39 | 33 |
| sO2 | % | 55 | 67 | 69 | 39 | 76 | 59 | 73 | 76 | 66 |

Subject 2—Observed Response for Dose 1 AS: As shown in FIG. 6, venous pH was observed to rise from a borderline acidotic start at 7.392, towards alkaline at T=20, and then reduce back towards acidic at T=50. Although the AS solution should shift the blood stream towards acidic, this was not observed, perhaps because the observation point at T=20 occurred after renal compensation processes had already begun to manage acid-base status. At the same time, venous $HCO_{3-}$ was first measured to have a high value of 33.2 mmol/L, consistent with Cushing's disease. Over treatment, the values reduced to 31 mmol/L at the other time points, consistent with a flow to the intracellular or renal extraction. As shown in FIG. 7, venous $sO_2$ and $pO_2$ were observed to rise during this time, from low start levels at 55% $sO_2$ and 30 mm Hg $pO_2$, consistent with an enhanced servicing of oxygen to tissues. $pCO_2$ was seen to reduce, consistent with a reduction in metabolism, plasma volume expansion, or reduced hemoglobin affinity for $CO_2$, with heightened affinity for $O_2$.

Subject 2—Observed Response for Dose 4 ASVM: As shown in FIG. 8, venous pH was observed to rise towards alkaline at T=20, and then reduce back towards acidic at T=50, in a response that was similar to Dose 1 using AS. At the same time, venous $HCO_{3-}$ was observed at T=−5 to be 26.7 mmol/L, consistent with a Cushing's resolution, and largely unchanged throughout the observation period. As shown in FIG. 9, venous $sO_2$ and $pO_2$ were again observed to rise during drug administration, along with a reduction in $pCO_2$.

Subject 2—Observed Response for Dose 5 ASVM: As shown in FIG. 10, dose 5 provoked a response unlike doses 1 and 4, where venous pH was observed to drop towards acidic throughout the observation frame. This could be attributed to the more alkaline starting bias for the bloodstream. At the same time, venous $HCO_{3-}$ was observed at T=−5 to be 29.4 mmol/L, again consistent with a Cushing's resolution. Instead of rising or remaining unchanged, bloodstream $HCO_{3-}$ reduced throughout the observation period, consistent with flow into the intracellular. As shown in FIG. 11, venous $sO_2$ and $pO_2$ were observed to have higher start levels at 73% $sO_2$ and 37 mmHg $pO_2$, constant with a more durable restoration of enhanced servicing of oxygen to tissues. $sO_2$ and $pO_2$ were again observed to rise further during drug administration. $pCO_2$ remained largely unchanged. The difference in behavior at dose 5, relative to doses 1 and 4, is consistent with achievement of an enhanced homeostasis regarding acid/base status.

Subject 3 Doses 1 and 4 ASVM and Dose 5 AS: Observed Response: Blood pH, blood $HCO_{3-}$, and oximetry were observed at time intervals of 5 min pre-dose commencement (T=−5), 20 min post dose commencement (T=20), and 5 minutes post-dose complete (dose complete at T=45, measurement at T=50) as shown in Table 5.

Subject 3 Doses 1 and 4 ASVM and Dose 5 AS Observed Response: Blood pH, blood HCO3−, and oximetry were observed at time intervals of 5 min pre-dose commencement (T=−5), 20 min post dose commencement (T=20), and 5 minutes post-dose complete (dose complete at T=45, measurement at T=50) as shown in Table 9.

TABLE 9

Subject 3 Response for Dose 1 and 4 ASVM, Dose 5 AS

| | | ASVM Day 1 Dose 1 | | | ASVM Day 6 Dose 4 | | | AS Day 8 Dose 5 | | |
|---|---|---|---|---|---|---|---|---|---|---|
| Time | min | −5 | 20 | 50 | −5 | 20 | 50 | −5 | 20 | 50 |
| pH | — | 7.455 | * | * | 7.437 | 7.392 | 7.428 | 7.423 | 7.412 | 7.375 |
| cHCO3− | mmol/L | 32.5 | * | * | 27.1 | 27.3 | 27.7 | 26.2 | 26.0 | 25.5 |
| pCO2 | mmHg | 46.2 | * | * | 42.6 | 49.9 | 45.0 | 42.4 | 43.6 | 49.9 |
| pO2 | mmHg | 29 | * | * | 32 | 29 | 34 | 34 | 31 | 20 |
| sO2 | % | 57 | * | * | 67 | 57 | 69 | 70 | 64 | 34 |

* Sample not available

Subject 3—Observed Response for Dose 1, 4 ASVM: Not presented, materially similar to Subject 2.

Subject 3—Observed Response for Dose 5 AS: As shown in FIG. 12, dose 5 provoked a response similar to dose 5 in Subject 2, where venous pH was observed to drop towards acidic throughout the observation frame. At the same time, venous $HCO_{3-}$ was observed at T=−5 to be 27.7 mmol/L, again consistent with a Cushing's resolution. Instead of rising or remaining unchanged, bloodstream HCO3− reduced throughout the observation period, consistent with flow into the intracellular. As shown in FIG. 13, venous $sO_2$ and $pO_2$ were observed to have relatively high start levels at 70% $sO_2$ and 34 mm Hg $pO_2$, consistent with a biasing towards enhanced servicing of oxygen to tissues, relative to pre-treatment levels. In contrast to Subject 2's Dose 5 response using AS product, $sO_2$ and $pO_2$ responded to AS product infusion by dropping during drug administration, which is a stimulus that is recognized to have the potential to stimulate EPO release from the liver to promote RBC store supplementation. This difference in response could have been caused by the formulation differences between the AS and ASVM configurations. $pCO_2$ rose correspondingly during this time.

Subject 1 Dose 1, 4, 5 ASVM Data (Exhibited for completeness, Similar to Subject 2 and Subject 3): Blood pH, blood $HCO_{3-}$, and oximetry were observed at time intervals of 5 min pre-dose commencement (T=−5), 20 min post dose commencement (T=20), and 5 minutes post-dose complete (dose complete at T=45, measurement at T=50) as shown in Table 10.

TABLE 10

Subject 1 Response for ASVM Dose 1, 4, 5

| | | ASVM Day 1 Dose 1 | | | ASVM Day 6 Dose 4 | | | ASVM Day 8 Dose 5 | | |
|---|---|---|---|---|---|---|---|---|---|---|
| Time | min | −5 | 20 | 50 | −5 | 20 | 50 | −5 | 20 | 50 |
| pH | — | 7.444 | * | * | 7.426 | 7.435 | 7.448 | 7.429 | 7.447 | 7.431 |
| cHCO3− | mmol/L | 34.1 | * | * | 30.1 | 31.1 | 31.3 | 30.1 | 29.9 | 29.6 |
| pCO2 | mmHg | 49.7 | * | * | 50.8 | 50.5 | 48.5 | 49.6 | 45.8 | 47.7 |
| pO2 | mmHg | 30 | * | * | 24 | 29 | 35 | 36 | 37 | 36 |
| sO2 | % | 59 | * | * | 48 | 59 | 71 | 73 | 76 | 73 |

Results Section 2: Electrolyte, Hb, Glu, and Lac Response:

Subject 2 AS Dose 1 and ASVM Doses 4 and 5—Observed Response: Blood electrolytes, hemoglobin (Hb), Glucose (Glu) and Lactate (Lac) were observed at time intervals of 5 min pre-dose commencement (T=−5), 20 min post dose commencement (T=20), and 5 minutes post-dose complete (dose complete at T=45, measurement at T=50) as shown in Table 7.

TABLE 7

Subject 2 Response for ASVM Dose 4, 5

| | | ASVM Day 6 Dose 4 | | | ASVM Day 8 Dose 5 | | |
|---|---|---|---|---|---|---|---|
| Time | min | −5 | 20 | 50 | −5 | 20 | 50 |
| cK+ | mmol/L | 4.6 | 4.2 | 2.9 | 4.4 | 4.0 | 3.7 |
| cNa+ | mmol/L | 140.0 | 138.0 | 144.0 | 137.0 | 137.0 | 138.0 |
| cCa2+ | mmol/L | 1.7 | 1.7 | 1.6 | 1.7 | 1.6 | 1.6 |
| cCl− | mmol/L | 103.0 | 103.0 | 105.0 | 100.0 | 101.0 | 101.0 |
| ctHb | g/dL | 14.8 | 11.9 | 13.2 | 13.2 | 11.2 | 11.0 |
| cGlu | mg/dL | 105.0 | 115.0 | 99.0 | 91.0 | 83.0 | 89.0 |
| cLac | mmol/L | 1.3 | 0.7 | 0.3 | 0.4 | 0.5 | 0.5 |

Subject 2 ASVM Doses 4 and 5—Observed Hb Response and Inference of Plasma Volume Changes: Over the observation timeframe, Hb reduced from its start value, sometimes showing evidence of rebound during the observation period. This cannot be interpreted as hemolysis, as a rebound on this timescale would be impossible. The change in Hb concentration is consistent with a change in blood volume, likely due to a change in plasma volume. Such exchange is required during exercise-like stimulus to maintain vascular pressure, under conditions of vasodilation, where vascular volume increases.

Subject 2 ASVM Doses 4 and 5—Observed Glucose Response: Over the observation timeframe, Glucose was perturbed (up and down) from its start value, while showing evidence of rebound during the observation period. While the reduction could be attributable to increased blood volume, elevations in Glucose concentration cannot. Observed Glucose elevation is consistent with perturbation of glucose exchange, such as happens during exercise.

Subject 2 ASVM Doses 4 and 5—Observed Lactate Response: Over the observation timeframe, Lactate was observed to have a low presentation value, which further reduced in Dose 4, and elevated slightly in Dose 5. This is consistent with the lactate burden steadily dropping with successive doses, as improved perfusion increased aerobic metabolism, so as to resolve lactate debt. Elevated lactate was seen in Dose 5, despite s suspected plasma volume dilution. This is consistent with presentation of HCO3− into muscles to release stored lactate.

Subject 2 ASVM Doses 4 and 5—Observed Electrolyte Response: Over the observation timeframe, electrolyte exchange was observed. Potassium and Sodium were observed to drop during treatment, which could be attributed to increased plasma volume. It is consistent with a flow of $H^+$ into the cell, elevating the Chemiosmotic gradient to improve ATP yield and enhancing action of the Na/K ATPase to transport $K^+$ into the cell. At the same time, a reduction in bloodstream Calcium was observed. $H^+/Na^+$ exchange and K+/Na+ exchange would promote an elevation of bloodstream $Na^+$, to promote $Ca^{2+}$ exchange to the blood via the $Ca^{2+}/Na^+$ exchanger. Elevations in bloodstream $Cl^-$ were also observed during the observation period.

Results Section 4: Hematology, Chemistry, Endocrinology, and Serology:

Observed Response between Day 1 and Day 8 encompassing 4 doses in 3 horses: Hematology, Chemistry, Endocrinology, and Serology were observed on Day 1, before Dose 1, and on Day 8, before dose 5, thus encompassing 4 doses of ASVM, or in some dose instances, AS. The following effects can be observed in the data, as shown in Table 8.

White blood cell (WBC) and neutrophil counts were observed to drop for all subjects, consistent with an alleviation of the inflammation response.

Platelet counts and fibrinogen were observed to rise for all subjects, consistent with control over clotting cascade and reduced consumption of clotting products. It is also consistent with increased production of platelets in bone marrow upon resolution of Thrombocytopenia, and increased presentation of fibrinogen through enhanced liver function.

Creatinine was observed to rise in all subjects, consistent with an increase in muscle mass and improved capacity to store ATP in muscle as Phosphocreatine.

BUN:Creatinine ratio was observed to fall for all subjects, consistent with increased flow through the kidneys.

$Ca^{2+}$ and $K^+$ were observed to drop for all subjects, consistent with intracellular uptake of $K^+$ via $Na^+/K^+$ ATPase, and renal extraction of $Ca^{2+}$, so as to reduce bloodstream presentation. Reductions in $Ca^{2+}$ and increases in $K^+$ could have the potential to reduce chemiosmotic gradient dependence on $Ca^{2+}$ so as to restore electron chain transport function, reduce corresponding ROS corresponding to the electron chain transport, and increase basal metabolic rate. A reduction in intracellular calcium, along with ROS reduction and alkaline conditions and elevated $Mg^{2+}$, would also have the potential to improve peroxisome function to restore long-chain fatty acid reduction for metabolic use, increased capacity to repair myelin for enhanced nerve function, and improving catalase servicing from the peroxisome. Additionally lower $Ca^{2+}$ could restore eNOS function by reducing caveolae bound Caveolin to allow eNOS to translocate from the Golgi back to the membrane caveolae. Lower intracellular calcium could also signal more M2 prenotype presentation for macrophages, microglia, and osteoblasts among others. Increased $K^+$ could act to enhance muscle function and nerve transmission, reduce cramping of muscles, and provide other benefits.

Creatine kinase was observed to drop for all subjects, consistent with a potential increase of consumption of creatine kinase in enzymatic action to promote storage of ATP with creatine as Phosphocreatine to enhanced stored energy in muscles. Alternately, the reduction in blood plasma can indicate a reduction in the ongoing rate of tissue damage, such as in myocardial infarction (heart attack), rhabdomyolysis (severe muscle breakdown), muscular dystrophy, autoimmune myositides, and acute kidney injury, so as to minimize presentation of damaged tissue contents to the bloodstream.

Total T4 was observed to rise for all subjects, potentially indicating improved thyroid function to produce more thyroxine. This, among other things, is associated with increases in synthesis of $Na^+/K^+$ ATPases, glucose absorption, gycogenolysis, gluconeogenesis, lipolysis, protein synthesis, net catabolic degradation, cardiac beta-1 receptors for enhanced sympathetic nervous control, and basal metabolic rate.

Equine endogenous ACTH was observed to fall for all subjects, consistent with a reduction in cortisol levels, so as to promote calming and anti-anxiety effects. Additionally consistent with promoting resolution of Cushing's disease.

Lyme's antibodies were shown to reduce in ratio presentation, as indicated by a smaller divisor. This is consistent with resolution of Lyme's disease and progression towards immune quiescing, with reduction of inflammation response.

Lyme's proteins were observed to increase in presentation, consistent with enhanced action of plasmin during alkaline rebound phases, which could reduce the fibrin layer associated with borrelia, so as to expose its surface proteins.

TABLE 8

| | | Subject 1 | | Subject 2 | | Subject 3 | | |
|---|---|---|---|---|---|---|---|---|
| Patient Test | Notes | 14-Nov Pre-sample | 21-Nov Post-sample | 14-Nov Pre-sample | 21-Nov Post-sample | 14-Nov Pre-sample | 21-Nov Post-sample | Reference Values |
| HEMATOLOGY | | | | | | | | |
| WBC | | 6.1 | 4.4 | 7.8 | 7.2 | 8.9 | 9.0 | 4.3-11.4 K/uL |
| Neutrophils | | 3.251 | 2.275 | 3.962 | 3.168 | 3.382 | 4.329 | 2.46-7.23 K/uL |
| Platelets | | 106 | 141 | 129 | 192 | 148* | 198 | 70-250 K/uL |
| Fibrinogen | | 116 | 127 | 129 | 168 | 131 | 147 | 135-249 mg/dL |
| CHEMISTRY | | | | | | | | |
| Creatinine | | 0.7 | 0.9 | 1.2 | 1.4 | 1.2 | 1.4 | 0.8-1.8 mg/dL |
| BUN:Creatinine Ratio | | 30.0 | 23.3 | 10.8 | 10.0 | 11.7 | 7.9 | |
| Calcium | | 13.0 | 11.6 | 12.4 | 11.6 | 12.2 | 11.6 | 10.2-12.8 mg/dL |
| Sodium | | 136 | 136 | 136 | 137 | 136 | 137 | 132-141 mmol/L |
| Potassium | | 4.8 | 4.1 | 5.2 | 3.7 | 5.4 | 3.9 | 2.5-5.2 mmol/L |
| Creatine Kinase | | 334 | 221 | 271 | 210 | 349 | 259 | 130-497 U/L |
| ENDOCRINOLOGY | | | | | | | | |
| Total T4 | | 1.5 | 1.8 | 2.5 | 3 | 1.7 | 2.6 | 1-3.8 ug/dL |
| Equine Endogenous ACTH | a3 | 26 | 24 | 19 | 18 | 26 | 16 | 9-35 pg/mL |
| SEROLOGY | | | | | | | | |
| Lyme Antibody by IFA | a4 | Positive @ 1:3200 | Positive @ 1:800 | Positive @ 1:800 | Positive @ 1:200 | Positive @ 1:800 | Positive @ 1:200 | |
| Lyme OspA | | 123 negative | 129 negative | 197 negative | 242 negative | 225 negative | 201 negative | |

TABLE 8-continued

Hematology, Chemistry, Endocrinology, and Serology Evolving Over 4 doses in 7 days

| Patient Test | Notes | Subject 1 14-Nov Pre-sample | Subject 1 21-Nov Post-sample | Subject 2 14-Nov Pre-sample | Subject 2 21-Nov Post-sample | Subject 3 14-Nov Pre-sample | Subject 3 21-Nov Post-sample | Reference Values |
|---|---|---|---|---|---|---|---|---|
| Lyme OspC | | 73 negative | 77 negative | 238 negative | 272 negative | 79 negative | 69 negative | |
| Lyme OspF | b2 | 3000 positive | 3963 positive | 318 negative | 390 negative | 464 negative | 498 negative | |
| *Ehrlichia canis* Antibody | c2 | Negative | Positive @ 1:100 | Negative | Negative | Negative | Negative | |

Notes:
a3-Significant variations in endogenous ACTH concentration associated with the season have been reported. An endogenous ACTH measured between November and July of >35 pg/mL is consistent with equine Cushing's disease (PPID). Cases with early PPID may fail to demonstrate significant elevations in resting ACTH concentrations during these months. Retesting resting ACTH levels during August and October, when test sensitivity is highest, or performing a TRH stimulation test (December to June) is recommended. Between August and October, an endogenous ACTH concentration of >100 pg/mL is consistent with equine Cushing's disease.
a4-Interpretation: if your result is negative, the interpretation is "No antibody present @1:100"; positive @(titer), the interpretation is 'Antibody present @(titer).
b2-Cornell no longer offers the Lyme Western Blot test. In its place they are offering the Lyme Equine Multiplex.
Lyme Disease Equine-Multiplex: The Lyme multiplex assay determines antibodies to three antigens, called outer surface proteins (Osp), of *B. burgdorferi* which have been shown to correlate with vaccinal antibodies, or acute and chronic stages of Lyme disease.
Negative: Negative values for antibodies to all three Osp antigens are predictive that the horse is not infected. If only one or two values are in the negative range see interpretation for equivocal or positive values for the corresponding Osp antigen.
Equivocal: Equivocal values can indicate very early infection or can be induced by non-specific serum reactions. If there are no positive values for any of the three Osp antigens, the horse should be retested in 2-3 weeks to confirm or exclude early infection. If one or two values are in the positive range see interpretation for positive values for that corresponding Osp antigen.
Positive/OspA (>2000): Positive values for antibodies to OspA are typically observed in vaccinated animals. In horses, however, antibodies to OspA also seem to rise during infection. Thus, the interpretation of results on antibodies to OspA is more complex in horses. If antibodies to OspC and/or OspF are positive, along with OspA, the horse should be considered as infected with *B. burgdorferi*.
Positive/OspC (>1000): Positive values for antibodies to OspC only are indicative for early infection. Antibody values for OspA can also be elevated during early infection.
Positive/OspF (>1250): Positive values for antibodies to OspF only are predictive for chronic infection stages. Positive values for antibodies to OspC and OspF in the same sample are indicators for an infection that occurred several weeks ago and is moving towards the chronic stage. Referral test performed at Cornell University.
c2-Interpretation: If your result is: The interpretation is: NEGATIVE No antibody present @1:25; POSITIVE @(titer) Antibody present @(titer). Positive samples are tested in incremental dilutions to 1:3200. Titers beyond 1:3200 are usually of limited clinical value. If you wish an endpoint titer there is an additional charge. A positive titer indicates exposure to *E. canis* or similar antigen but does not confirm the presence of disease. A CBC is recommended to identify abnormalities consistent with infection. If confirmation of infection is desired, *Ehrlichia* PCR test, code 2634 can be useful, especially in clinically sick animals.

The invention claimed is:

1. A method of elevating blood oxygen in a subject suffering from hypoxia, the method comprising elevating the pO2 in the blood in the subject suffering hypoxia, comprising administering to the subject a stable therapeutic composition comprising an intravenous buffer solution comprising an equilibrium product of mixing at least one pharmaceutical grade acid with at least one pharmaceutical grade pH buffering agent in a sterile aqueous solution,
wherein the pharmaceutical grade acid is selected from the group consisting of hydrochloric acid, ascorbic acid, dehydroascorbic acid, acetic acid, citric acid, lactic acid, phosphoric acid, and a combination of two or more thereof,
wherein the composition is administered in an amount effective to provide metabolic corrections that promote vasodilation, reduction of intracellular accrual of $Ca^{2+}$, or stimulate renal and respiratory action to shift blood pH towards alkaline, thereby elevating the subject's blood oxygen to alleviate the hypoxia,
wherein the concentration of the pharmaceutical grade acid and the pharmaceutical grade pH buffering agent in the buffer solution is sufficient to provide a total titratable acid content of from 60 mmol/L to 3,000 mmol/L when administered to a subject, and
wherein the selection of the pharmaceutical grade acid and the pharmaceutical grade pH buffering agent is effective to provide a buffer solution pH of between 4 and 7.7.

2. The method of claim 1, wherein the buffer solution is administered in an effective amount that is sufficient to reduce the physiological bloodstream pH of a subject by 0.01 to 1.1.

3. The method of claim 1, wherein the buffer solution is sufficient to reduce the physiological bloodstream pH of a subject by 0.15 to 0.75.

4. The method of claim 1, wherein the buffer solution has a buffer capacity sufficient to sustain the reduction of the physiological bloodstream pH of the subject for between 1 minute and 1 week.

5. The method of claim 1, wherein the composition further comprises one or more of a magnesium ion source, a potassium ion source, and a calcium ion source.

6. The method of claim 1, wherein the composition further comprises one or more of a B vitamin, vitamin C, and a K vitamin.

7. The method of claim 1, wherein the subject is a human or veterinary subject.

8. The method of claim 1, wherein the buffer solution is sufficient to reduce the physiological bloodstream pH of a subject by 0.15 to 0.5.

9. The method of claim 1, wherein the buffer solution has a buffer capacity sufficient to sustain the reduction of the physiological bloodstream pH of the subject for between 1 minute and 1 hour.

10. The method of claim 1, wherein the buffer solution has a buffer capacity sufficient to sustain the reduction of the physiological bloodstream pH of the subject for between 1 hour and 1 day.

11. The method of claim 1, wherein the buffer solution has a buffer capacity sufficient to sustain the reduction of the physiological bloodstream pH of the subject for between 1 day and 1 week.

12. The method of claim 1, wherein the pharmaceutical grade acid is selected from the group consisting of hydrochloric acid, ascorbic acid, acetic acid, dehydroascorbic acid, and a combination thereof.

13. The method of claim 1, wherein the pharmaceutical grade pH buffering agent is a bicarbonate.

14. The method of claim 1, wherein the pharmaceutical grade pH buffering agent is selected from the group consisting of a bicarbonate, sodium bicarbonate, a phosphate buffer, sodium hydroxide, organic acid, organic amine, ammonia, citrate buffer, tris-hydroxymethyl amino methane, a synthetic buffer, and a combination thereof.

15. The method of claim 1, wherein said composition comprises 840±84 mg of sodium bicarbonate as said pharmaceutical grade buffering agent, 4.5±0.45 mM of hydrochloric acid, and 900±90 mg of L Ascorbic acid or 100±10 mg of dehydroascorbic acid, or both, as said pharmaceutical grade acid, and per quantity of water sufficient to obtain a final composition volume of 20 mL.

16. The method of claim 1, wherein said composition further comprises:
900±90 mg of L-Ascorbic Acid;
63.33±6.33 mg Thiamine HCl;
808±80.8 mg of Magnesium Sulfate;
1.93±0.193 mg of Cyanocobalamin;
119±11.9 mg of Niacinamide;
119±11.9 mg of Pyridoxine HCl;
2.53±0.253 mg of Riboflavin 5'Phosphate; and
2.93±0.293 mg of Calcium D-Pantothenate
per quantity of water sufficient to obtain a final composition volume of 20 mL.

17. The method of claim 1, wherein the intravenous buffer solution comprises a bicarbonate ion ($HCO_3^-$) concentration between about 0.5 and about 2.0 M/L.

18. The method of claim 1, wherein the intravenous buffer solution further comprises an antioxidant defense compound selected from the group consisting of a nonenzymatic compound or an enzymatic compound.

19. The method of claim 18, wherein the nonenzymatic compound is selected from the group consisting of tocopherol (aTCT), coenzyme Q10 (Q), cytochrome c (C), glutathione (GSH) and a combination thereof.

20. The method of claim 18, wherein the enzymatic compound is selected from the group consisting of manganese superoxide dismutase (MnSOD), catalase (Cat), glutathione peroxidase (GPX), phospholipid hydroperoxide glutathione peroxidase (PGPX), glutathione reductase (GR), peroxiredoxin (PRX3/5), glutaredoxin (GRX2), thioredoxin (TRX2), thioredoxin reductase (TRXR2), and a combination thereof.

21. The method of claim 1, wherein the intravenous buffer solution is in a hypotonic, isotonic or hypertonic form.

22. The method of claim 1, wherein the hypoxia is associated with a heart attack, cardiovascular disease, a lung condition, concussive cascade, reperfusion injury, myocardial infarction, diabetes or tissue trauma.

23. The method of claim 1, wherein said composition further comprises one or more ingredients selected from the group consisting of vitamins, salts, acids, amino acids or salts thereof, and stabilized oxidative species.

24. The method of claim 1, wherein said pharmaceutical grade acid comprises ascorbic acid.

25. The method of claim 1, wherein said pharmaceutical grade acid comprises dehydroascorbic acid.

26. The method of claim 1, wherein said composition is lyophilized or frozen.

27. The method of claim 1, wherein said composition is stored in a spectral-blocking vial.

28. The method of claim 1, wherein said composition is formed by combining components from two or more vials.

* * * * *